United States Patent
Gressard et al.

(10) Patent No.: US 11,633,472 B2
(45) Date of Patent: Apr. 25, 2023

(54) COMPOSITIONS

(71) Applicant: GLAXOSMITHKLINE BIOLOGICALS, S.A., Rixensart (BE)

(72) Inventors: Herve Gressard, Rixensart (BE); Pierre Sae Houer, Wavre (BE); Laurent Strodiot, Rixensart (BE)

(73) Assignee: GlaxoSmithKline Biologicals SA

( * ) Notice: Subject to any disclaimer, the term of this patent is extended or adjusted under 35 U.S.C. 154(b) by 0 days.

(21) Appl. No.: 16/327,774

(22) PCT Filed: Aug. 30, 2017

(86) PCT No.: PCT/EP2017/071756
§ 371 (c)(1),
(2) Date: Feb. 22, 2019

(87) PCT Pub. No.: WO2018/041891
PCT Pub. Date: Mar. 8, 2018

(65) Prior Publication Data
US 2019/0175729 A1    Jun. 13, 2019

(30) Foreign Application Priority Data

Sep. 1, 2016  (GB) .................................... 1614799

(51) Int. Cl.
*A61K 39/39*  (2006.01)
*A61K 39/12*  (2006.01)
*A61K 39/15*  (2006.01)
*A61K 39/00*  (2006.01)

(52) U.S. Cl.
CPC .............. *A61K 39/39* (2013.01); *A61K 39/12* (2013.01); *A61K 39/15* (2013.01); *A61K 2039/525* (2013.01); *A61K 2039/542* (2013.01); *A61K 2039/55505* (2013.01); *A61K 2039/55511* (2013.01); *C12N 2720/12334* (2013.01)

(58) Field of Classification Search
CPC ........ A61K 39/39; A61K 39/12; A61K 39/15; A61K 2039/525; A61K 2039/542; A61K 2039/55505; A61K 2039/55511; C12N 2720/12334
See application file for complete search history.

(56) References Cited

U.S. PATENT DOCUMENTS

| 8,192,747 | B2 * | 6/2012 | Vande Velde | A61K 39/12 424/215.1 |
| 8,821,891 | B2 * | 9/2014 | Vande Velde | A61P 1/04 424/215.1 |
| 2003/0065024 | A1 * | 4/2003 | Lambert | A61K 9/1075 514/449 |
| 2005/0048083 | A1 * | 3/2005 | Colau | A61K 39/12 424/215.1 |
| 2008/0057082 | A1 * | 3/2008 | Colau | C07K 14/005 424/215.1 |
| 2008/0181914 | A1 * | 7/2008 | Eichhorn | A61K 39/145 424/209.1 |
| 2012/0237547 | A1 * | 9/2012 | Vande Velde | A61P 31/14 424/215.1 |
| 2014/0271593 | A1 * | 9/2014 | Bromley | A23L 33/105 424/94.1 |
| 2015/0098967 | A1 * | 4/2015 | Vadrevu | A61K 39/39 424/215.1 |

FOREIGN PATENT DOCUMENTS

| CN | 103751107 A | * | 4/2014 | |
| WO | 2006087205 A1 | | 8/2006 | |
| WO | 2007132480 A2 | | 11/2007 | |
| WO | 2011007363 A1 | | 1/2011 | |
| WO | WO-2012103464 A2 | * | 8/2012 | ........... A61K 9/1652 |
| WO | WO-2012145739 A1 | * | 10/2012 | ........... A61K 47/46 |
| WO | 2015048115 A1 | | 4/2015 | |

OTHER PUBLICATIONS

Vesikari T. Rotavirus vaccination: a concise review. Clin Microbiol Infect. Oct. 2012;18 Suppl 5:57-63. Epub Aug. 6, 2012.*
Groome MJ, Koen A, Fix A, Page N, Jose L, et al. Safety and immunogenicity of a parenteral P2-VP8-P[8] subunit rotavirus vaccine in toddlers and infants in South Africa: a randomised, double-blind, placebo-controlled trial. Lancet Infect Dis. Aug. 2017;17(8):843-853. Epub May 5, 2017.*
Brandau DT, Jones LS, Wiethoff CM, Rexroad J, Middaugh CR. Thermal stability of vaccines. J Pharm Sci. Feb. 2003;92(2):218-31.*
Morefield GL. A rational, systematic approach for the development of vaccine formulations. AAPS J. Jun. 2011;13(2):191-200. Epub Feb. 23, 2011.*
Peterson SE, Wang S, Ranheim T, Owen KE. Citrate-mediated disaggregation of rotavirus particles in RotaTeq vaccine. Antiviral Res. Feb. 2006;69(2):107-15. Epub Nov. 21, 2005.*
Dias JA, Thillainayagam AV, Hoekstra H, Walker-Smith JA, Farthing MJ. Improving the palatability of oral rehydration solutions has implications for salt and water transport: a study in animal models. J Pediatr Gastroenterol Nutr. Oct. 1996;23(3):275-9.*
Gad S, ed. "Pharmaceutical Manufacturing Handbook: Production and Processes". Pub. Aug. 28, 2007. John Wiley & Sons, Inc. Hoboken, New Jersey, USA . . . (Year: 2007).*
Peterson SE, Wang S, Ranheim T, Owen KE. Citrate-mediated disaggregation of rotavirus particles in RotaTeq vaccine. Antiviral Res. Feb. 2006;69(2):107-15. Epub Nov. 21, 2005. (Year: 2005).*
Hasija M, Li L, Rahman N, Ausar SF. Forced degradation studies: an essential tool for the formulation development of vaccines. Vaccine: Development and Therapy. 2013;3:11-33. (Year: 2013).*
Strickley RG. Solubilizing excipients in oral and injectable formulations. Pharm Res. Feb. 2004;21(2):201-30. (Year: 2004).*

* cited by examiner

Primary Examiner — Rachel B Gill
(74) Attorney, Agent, or Firm — Dana L. Broughton

(57) ABSTRACT

The disclosure defined by this invention is an immunogenic composition comprising a viral antigen, a sugar and/or polyol, an adipate buffer, calcium ions and/or magnesium ions, and one or more positively charged amino acids.

11 Claims, 13 Drawing Sheets

COMPOSITIONS

FIELD OF THE INVENTION

The present invention relates to novel viral compositions that are useful as pharmaceutical compositions and vaccines, to methods for preparing them and to their use in preventing and treating viral infections.

BACKGROUND OF THE INVENTION

Acute, infectious diarrhoea is a leading cause of disease and death in many areas of the world. In developing countries, the impact of diarrhoeal disease is very important. For Asia, Africa and Latin America, it has been estimated that there are between 3-4 billion cases of diarrhoea each year and of those cases about 5-10 million result in death (Walsh, J. A. et al.: *N. Engl. J. Med.,* 301:967-974 (1979)).

Rotaviruses have been recognised as one of the most important causes of severe diarrhoea in infants and young children (Estes, M. K. Rotaviruses and Their Replication in Fields Virology, Third Edition, edited by Fields et al., Raven Publishers, Philadelphia, 1996). It is estimated that rotavirus disease is responsible for over 600,000 deaths annually. Rotavirus-induced illness most commonly affects children between 6 and 24 months of age, and the peak prevalence of the disease generally occurs during the cooler months in temperate climates, and year-round in tropical areas. Rotaviruses are typically transmitted from person to person by the faecal-oral route with an incubation period of from about 1 to about 3 days. Unlike infection in the 6-month to 24-month age group, neonates are generally asymptomatic or have only mild disease. In contrast to the severe disease normally encountered in young children, most adults are protected as a result of previous rotavirus infection so most adult infections are mild or asymptomatic (Offit, P. A. et al. *Comp. Ther.,* 8(8):21-26, 1982).

The development of viral, including rotavirus, formulations must comply with a number of requirements, including worldwide distribution potential and stability under a broad range of environmental and storage conditions. In particular, the stability of a formulation, especially of a pharmaceutical or vaccine composition, will in general be better at lower temperatures compared to room or higher temperatures.

Therefore, there is a need for thermostable viral vaccine formulations, including rotavirus, which substantially retain their potency at room temperature or higher and which can be afforded by low income and developing world countries. Compositions of the present invention may have increased thermostability for a longer duration and/or increased thermostability at higher temperatures compared to compositions of the prior art.

SUMMARY OF THE INVENTION

The inventors have found that the addition of one or more positively charged amino acids to a viral vaccine composition comprising a sugar and/or polyol, an adipate buffer, calcium ions and/or magnesium ions, results in a surprising improvement in thermostability.

Thus, in one aspect, the present invention provides an immunogenic composition comprising:
  a viral antigen such as a live attenuated rotavirus,
  a sugar and/or polyol,
  an adipate buffer,
  calcium ions and/or magnesium ions, and
  one or more positively charged amino acids.

In another aspect, there is provided an immunogenic composition according to the above compositions, for use as a medicament, such as for use in the treatment or prevention of viral, such as rotavirus, infection; a method for the treatment or prevention of viral, such as rotavirus, infection comprising administering the above immunogenic composition to a subject having or at risk of infection; a method for the preparation of a viral, such as a rotavirus, vaccine comprising admixing the above components, and a method of preventing rotavirus infection and/or rotavirus-caused disease by administering such a vaccine to a subject in need thereof.

DETAILED DESCRIPTION OF THE INVENTION

Figure 1:
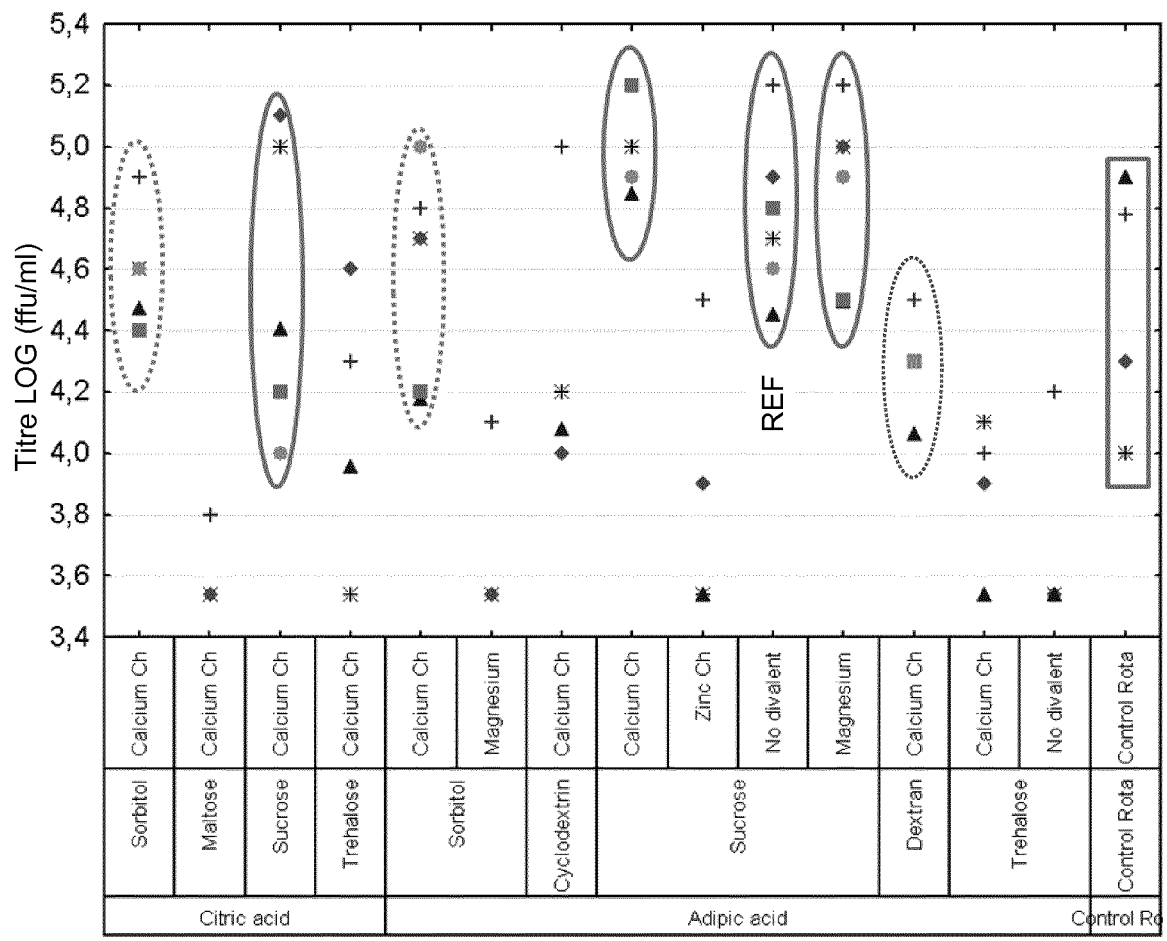
FIG. 1—Thermostability impact of different buffers, divalent cations and sugars/polyols after 7 days at 45° C.

In one aspect of the invention, there is provided an immunogenic composition comprising:
  a viral antigen,
  a sugar and/or polyol,
  an adipate buffer,
  calcium ions and/or magnesium ions, and
  one or more positively charged amino acids.

In a preferred embodiment, the viral antigen is a rotavirus antigen, for example a live, live attenuated, reassortant or inactivated rotavirus.

Suitably, the viral antigen is a live, live attenuated, reassortant or inactivated virus. In a preferred embodiment, the viral antigen is a live attenuated virus. In a more preferred embodiment, the viral antigen is a live attenuated rotavirus. In a most preferred embodiment, the viral antigen is a human live attenuated rotavirus.

Positively charged amino acids include histidine, arginine and lysine. Preferably, the one or more positively charged amino acids are selected from histidine and/or arginine.

In a preferred embodiment, the immunogenic composition comprises a live attenuated rotavirus, sucrose, adipic acid, calcium ions and histidine.

In another preferred embodiment, the immunogenic composition comprises a live attenuated rotavirus, sucrose, adipic acid, calcium ions and arginine.

In another preferred embodiment, the immunogenic composition comprises a live attenuated rotavirus, sucrose, adipic acid, magnesium ions and arginine.

In another preferred embodiment, the immunogenic composition comprises a live attenuated rotavirus, sucrose, adipic acid, magnesium ions and histidine.

Live Attenuated Viral Vaccines

Vaccines comprising live attenuated virus as the antigenic component are known in the art. Attenuated strains of viruses suitable for use in vaccines are known, including strains of adenovirus (e.g., adenovirus type 4, adenovirus type 7), herpes zoster (shingles), measles, mumps, rubella, influenza (e.g., seasonal flu nasal spray, 2009 H1N1 flu nasal spray), varicella (chicken pox), polio, rabies, virus, vaccinia (smallpox) and yellow fever virus. As used herein, a live attenuated virus is one that replicates in a suitable host, but where the disease-causing capacity has been decreased by biological or technical methods. Methods of attenuating virus are known in the art, such as passaging in cell culture, preparing reassortant virus, or using a variant from one species to vaccinate a subject of a different species. Live attenuated virus suitable for use in vaccines are capable of eliciting a protective immune response in the intended subject.

Rotavirus

Rotaviruses are spherical, and their name is derived from their distinctive outer and inner or double-shelled capsid structure. Typically, the double-shelled capsid structure of a rotavirus surrounds an inner protein shell or core that contains the genome. The genome of a rotavirus is composed of 11 segments of double-stranded RNA which encode at least 11 distinct viral proteins. Two of these viral proteins designated as VP4 (P protein) and VP7 (G protein) are structural proteins arranged on the exterior of the double-shelled capsid structure. The inner capsid of the rotavirus presents one protein, which is the rotavirus protein designated VP6. The relative importance of these three particular rotavirus proteins in eliciting the immune response that follows rotavirus infection is not yet clear. Nevertheless, the VP6 protein determines the group and subgroup antigen, and VP4 and VP7 proteins are the determinants of serotype specificity.

To date, at least 14 rotavirus G serotypes and 11 rotavirus P serotypes have been identified (Linhares A. C. & Bresse J. S., Pan. Am. J. Publ. Health 2000, 9, 305-330). Among these, 10 G serotypes and 6 P serotypes have been identifed among the human rotavirus.

VP7 protein is a 38,000 MW glycoprotein (34,000 MW when non-glycosylated) which is the translational product of genomic segment 7, 8 or 9, depending on the strain. This protein stimulates formation of the major neutralising antibody following rotavirus infection. VP4 protein is a non-glycosylated protein of approximately 88,000 MW which is the translational product of genomic segment 4. This protein also stimulates neutralising antibody following rotavirus infection. Since VP4 and VP7 proteins are the viral proteins against which neutralising antibodies are directed, they are believed to be prime candidates for development of rotavirus vaccines, affording protection against rotavirus illness.

Natural rotavirus infection during early childhood is known to elicit protective immunity.

Early vaccine development for preventing rotavirus infections began in the 1970s after the discovery of the virus. Initially, attenuated strains from animals and humans were studied, whilst more recent efforts have focused on human-animal reassortants.

ROTARIX™ is an oral vaccine used for the prevention of rotavirus gastroenteritis caused by G1 and certain non-G1 types; it is a live, attenuated rotavirus vaccine derived from the human 89-12 strain which belongs to the G1P[8] type. ROTARIX™ is available as a container of lyophilized vaccine that is reconstituted with a liquid diluent prior to oral application, and is suitable for use in human infants. It is recommended that both the lyophilized vaccine component and the diluents be stored refrigerated at 2° to 8° C. (36° to 46° F.).

It is known that many vaccines must be stored and transported at refrigeration temperatures maintained at 2° C. to 8° C. Further, it is also known that many vaccines must be administered immediately on being removed from refrigeration. This necessitates strict cold chain storage and transport which is problematic particularly in the developing and low income regions where the cold chain required for maintaining vaccine potency and efficacy is imperfect, overburdened or nonexistent, resulting in vaccine being wasted.

One thermostabilisation method has been to develop vaccine formulations that can be stored frozen (−20° C. to −70° C.) or alternatively to develop lyophilised vaccines that can be kept for a prolonged period of time at around refrigerator temperature (2° C. to 8° C.). However, it is a known fact that the lyophilisation process has a limiting capacity, and is associated with a high production cost. Furthermore, administering lyophilised vaccines may require more complex, hence relatively expensive, devices such as multichamber/vial vaccines, with the active ingredient in one chamber and the reconstitution liquid in another chamber. Lyophilised vaccines are also associated with higher shipment and storage cost. These options may be inadequate for some countries in the developing world where the administration device has to be affordable and where the availability of production and storage infrastructure may be non existent or unreliable.

Improving rotavirus vaccine formulation thermostability could impact all three of the following goals (Karp et al., Vaccine 2015 33(30):3471-3479): (i) development of fully thermostable vaccines could increase coverage by enabling the stocking of vaccines at facilities that do not have cold chain equipment and by facilitating outreach; (ii) the development of such vaccines might improve efficacy by decreasing the probability of administering vaccines whose efficacy was impaired by heat and/or freeze exposure and (iii) total system costs could be reduced by decreasing vaccine wastage due to detected heat and freeze exposures, by decreasing the cold chain footprint, and by reducing the overall requirements for the vaccine delivery supply chain.

International patent application number WO2009042202 discloses formulations for stabilisation of rotavirus and methods for stabilising viruses in liquid and dried formulations. In particular, formulations are provided including $Zn^{2+}$ cations which may stabilise the viability of rotaviruses.

Composition Components

Rotavirus

The composition of the present invention comprises a viral antigen, preferably a virus, such as a rotavirus. In particular the composition is an immunogenic composition, e.g. a vaccine composition. A rotavirus is understood to mean any rotavirus that is suitable for use in a vaccine formulation, e.g., a vaccine for administration to humans. Oral live rotavirus are especially contemplated. For example, any suitable rotavirus can be selected from the group consisting of: a live attenuated rotavirus from animals or humans, in particular a human live attenuated rotavirus; a reassortant rotavirus, in particular but not limited to a human-human reassortant rotavirus, a bovine-human reassortant rotavirus or a rhesus monkey-human reassortant rotavirus.

All rotavirus strains, human or animal strains, are contemplated in the present invention. Human rotavirus strains are especially suitable. In particular, the rotavirus is in one embodiment an attenuated human rotavirus, and the composition comprises a single variant or substantially a single variant, said variant being defined by the nucleotide sequence encoding at least one of the major viral proteins designated as VP4 and VP7 as disclosed in WO 01/12797, in particular any, including one or more, of the variants defined by the mutations set forth in Table 2, Tables 3.1 and 3.2 of WO 01/12797. In specific embodiments, the rotavirus antigen is any of the following live attenuated human rotavirus (HRV) strains: HRV 89-12C2 strain deposited under accession number ATCC VR 2272 (as described in EP 0 557 427), its progeny, reassortants and immunologically active derivatives thereof; HRV P43 strain deposited under accession number ECACC 99081301 (as described in WO 01/12797), its progeny, reassortants and immunologically active derivatives thereof. Suitably the rotavirus is present in the composition of the invention at a titre ranging from about $1 \times 10^5$ to about $1 \times 10^8$ pfu/mL.

Rotavirus belonging to strains which have the characteristics of any of the above mentioned deposited strains are also suitable vaccine strains. Derivatives from said deposited strains can be obtained by subjecting said strains to further processing such as by propagating them by further passaging, cloning, or other procedures using the live virus or by modifying said deposited strains in any way including by genetic engineering techniques or reassortant techniques. Such steps and techniques are well known in the art. Rotavirus of particular interest are progeny of any of said deposited strains and immunologically active derivatives thereof. Immunologically active derivatives means materials obtained from or with any of the deposited strains, in particular from or with HRV P43 strain deposited under accession number ECACC 99081301.

Of particular interest are reassortant rotaviruses which comprise at least one antigen or at least one segment of any of said deposited strains, for example reassortants which comprise a virulent strain of rotavirus in which one or part of one of the 11 genome segments has been replaced by the genome segment or part thereof of any of said deposited strains. Specifically, a rotavirus reassortant in which the segment or partial segment coding for NSP4 is a segment or partial segment of any of said deposited strains, may have useful properties. Reassortant rotaviruses and techniques for preparing them are well known (Foster, R. H. and Wagstaff, A. J. Tetravalent Rotavirus Vaccine, a review. ADIS drug evaluation, BioDrugs, Gev, 9 (2), 155-178, 1998).

The rotavirus used in the compositions of the present invention may be produced according to routine production techniques. Typically rotavirus antigen preparations may be derived from tissue culture methods used to propagate the virus. Suitable cell substrates for growing the virus include for example dog kidney cells such as MDCK or cells from a clone of MDCK, MDCK-like cells, monkey kidney cells such as AGMK cells including Vero cells which are particularly suitable, other cells lines of monkey kidney origin such as BSC-1, LLC-MK2 and MA104, suitable pig cell lines, or any other mammalian cell type suitable for the production of rotavirus for vaccine purposes. Suitable cell substrates also include human cells e.g. MRC-5 cells. Suitable cell substrates are not limited to cell lines; for example primary cells are also included.

Also within the scope of the invention are admixtures of any of the above recited deposited strains with other rotavirus variants, for example other cloned variants or other reassortant rotavirus, or with other viruses in particular other attenuated viruses.

The rotavirus for inclusion in the compositions of the present invention can be a monovalent rotavirus strain, i.e. containing a single rotavirus strain, or be multivalent, i.e. containing at least two or more rotavirus strains.

Suitably the rotavirus is derived from the G1P[8] type. More suitably, the rotavirus is derived from the human 89-12 strain.

A particularly suitable immunogenic composition contains the attenuated HRV P43 strain ("RIX4414", as deposited under accession number ECACC 99081301, see WO 01/12797), suitably at a concentration of $10^5$-$10^6$ ffu (focus forming units) per dose (or equivalent to $10^{5.5}$-$10^{6.5}$ as expressed in $CCID_{50}$ (median Cell Culture Infective Dose) per dose).

The skilled person will understand that other readily available attenuated strains, from human or animal origin, that are obtainable from depository institutions are also suitable and may be used as substitutes for the recited deposited strains.

Positively Charged Amino Acid

Compositions according to the invention comprise one or more positively charged amino acids.

Positively charged amino acids include histidine, arginine and lysine.

Histidine (abbreviated as His or H; encoded by the codons CAU and CAC) is an α-amino acid that is used in the biosynthesis of proteins. It contains an α-amino group (which is in the protonated —$NH^{3+}$ form under biological conditions), a carboxylic acid group (which is in the deprotonated —$COO^-$ form under biological conditions), and a side chain imidazole, classifying it as a positively charged (at physiological pH) amino acid. Suitably, histidine salts, enantiomers and other variants of histidine may be used.

Arginine (abbreviated as Arg or R) encoded by the codons CGU, CGC, CGA, CGG, AGA, and AGG is an α-amino acid that is used in the biosynthesis of proteins. It contains an α-amino group (which is in the protonated —$NH^{3+}$ form under biological conditions), an α-carboxylic acid group (which is in the deprotonated —$COO^-$ form under biological conditions), and a side chain of a 3-carbon aliphatic straight chain capped by a complex guanidinium, classifying it as a charged (at physiological pH)amino acid. Suitably, arginine salts, enantiomers and other variants of arginine may be used.

Lysine (abbreviated as Lys or K; encoded by the codons AAA and AAG) is an α-amino acid that is used in the biosynthesis of proteins. It contains an α-amino group (which is in the protonated —$NH^{3+}$ form under biological conditions), an α-carboxylic acid group (which is in the deprotonated —$COO^-$ form under biological conditions), and a side chain lysyl (($CH_2$)4$NH_2$), classifying it as a positively charged (at physiological pH), aliphatic amino acid. Suitably, lysine salts, enantiomers and other variants of lysine may be used.

Suitably the one or more positively charge amino acid are present at a concentration of at least 0.01% w/v, more suitably at least 0.05% w/v, more suitably at least 0.1% w/v, more suitably at least 0.15% w/v, more suitably at least 0.2% weight/volume (w/v). Suitably the one or more positively charge amino acid are present at a concentration of about or exactly 0.2% w/v.

Suitably the one or more positively charge amino acid are present at a concentration from about 0.01% w/v, 0.05% w/v, or 0.1% w/v, to about 1% w/v, 0.5% w/v, or 0.3% w/v. Suitably the histidine is present at a concentration of from about 0.01% to about 1% w/v, more suitably from about 0.05% to about 0.5% w/v, more suitably from about 0.1% w/v to about 0.3% w/v.

In a preferred embodiment, the positively charged amino acid are selected from histidine and/or arginine.

Suitably the histidine is present at a concentration of at least 0.01% w/v, more suitably at least 0.05% w/v, more suitably at least 0.1% w/v, more suitably at least 0.15% w/v, more suitably at least 0.2% weight/volume (w/v). Suitably the histidine is present at a concentration of about or exactly 0.2% w/v.

Suitably the histidine is present at a concentration from about 0.01% w/v, 0.05% w/v, or 0.1% w/v, to about 1% w/v, 0.5% w/v, or 0.3% w/v. Suitably the histidine is present at a concentration of from about 0.01% to about 1% w/v, more suitably from about 0.05% to about 0.5% w/v, more suitably from about 0.1% w/v to about 0.3% w/v.

Suitably the arginine is present at a concentration of at least 0.01% w/v, more suitably at least 0.05% w/v, more suitably at least 0.1% w/v, more suitably at least 0.15% w/v, more suitably at least 0.2% w/v. Suitably the arginine is present at a concentration of about or exactly 0.2% w/v.

Suitably the arginine is present at a concentration from about 0.01% w/v, 0.05% w/v, or 0.1% w/v, to about 1% w/v, 0.5% w/v, or 0.3% w/v. Suitably the arginine is present at a concentration of from about 0.01% w/v to about 1% w/v, more suitably from about 0.05% w/v to about 0.5% w/v, more suitably from about 0.1% w/v to about 0.3% w/v.

Suitably the composition comprises both histidine and arginine, suitably wherein each is present in any one of the concentration ranges specified above (i.e., the concentration of arginine and histidine may be the same or may differ within a composition).

Calcium Ions and/or Magnesium Ions

The composition according to the invention comprises calcium ions and/or magnesium ions.

Suitably the calcium ions are present at a concentration from about 0.5 mM, 1 mM, 3 mM or 5 mM, to about 7 mM, 15 mM, or 7 mM. Suitably the calcium ions are present at a concentration of from about 0.5 mM to about 20 mM, more suitably from about 1 mM to about 15 mM, more suitably from about 3 mM to about 7 mM, more suitably about or exactly 5 mM.

Suitably the calcium ions are present at a concentration of at least 1 mM, more suitably at least 3 mM, more suitably at least 4 mM, more suitably at least 5 mM.

Suitably the calcium ions are present in the form of calcium chloride.

Suitably when the composition of the invention comprises calcium ions, the composition also comprises histidine.

Suitably the magnesium ions are present at a concentration from about 0.5 mM, 1 mM, 3 mM or 5 mM, to about 7 mM, 15 mM, or 7 mM. Suitably the magnesium ions are present at a concentration of from about 0.5 mM to about 20 mM, more suitably from about 1 mM to about 15 mM, more suitably from about 3 mM to about 7 mM, more suitably about or exactly 5 mM.

Suitably the magnesium ions are present at a concentration of at least 1 mM, more suitably at least 3 mM, more suitably at least 4 mM, more suitably at least 5 mM.

Suitably the magnesium ions are present in the form of magnesium sulphate.

Suitably when the composition of the invention comprises magnesium ions, the composition also comprises arginine.

Suitably the composition comprises both calcium ions and magnesium ions, each in any one of the concentration ranges specified above (i.e., the concentration of arginine and histidine may be the same or may differ within a composition).

Suitably the composition comprises zinc ions. Suitably the zinc ions are present at a concentration of about 0.5 mM to about 20 mM. Suitably the zinc ions are present at a concentration of lower than 0.1 mM. Suitably the composition is substantially free of zinc ions.

Adipate Buffer

The composition according to the invention comprises an adipate buffer. Suitably the adipate buffer is a salt of adipic acid, e.g., monosodium salt of adipic acid, monopotassium salt of adipic acid, suitably disodium adipate or dipotassium adipate, or calcium adipate. More suitably, the adipate buffer is di-sodium adipate.

Suitably, the composition comprises adipate buffer at about 1% w/v, 3% w/v, 5% w/v or 7% w/v w/v, to about 8% w/v, 10% w/v, or 20% w/v, for example, from about 3% to about 10% w/v, more suitably about 5% to about 8% w/v, more suitably about 7% w/v adipate buffer.

It will be understood that the adipate concentration within the range mentioned above may be suitably adapted, through routine experimentation, according to the antacid capacity to be achieved and the volume of the vaccine dose.

Sugar/Polyol

The composition of the invention comprises one or more sugar(s) and/or polyol(s). Suitably the sugar(s) and/or polyol(s) is selected from the list consisting of: glycerol, erythrose, fucose, erythriol, xylitol, arabitol, ribose, dextrose, xylose, arabinose, glucose, tagalose, mannose, galactose, fructose, inositol, sorbitol, mannitol, galactitol, a combination of glucose and fructose, maltose, sophorose, lactose, cellobiose, melibiose, trehalose, sucrose, palatinose, maltulose, lactulose, maltitol, lactitol, raffinose, maltotriose, melezitose, cellotriose, ciritol, maltotetraose, stachyose, cellotetraose, maltopentaose, cellopentaose, maltohexaose, cellohexaose, dextran sulphate and α-cyclodextrin.

More suitably the sugar(s) and/or polyol(s) is selected from the list consisting of: sucrose, glucose, maltose, trehalose, fructose, α-cyclodextrin, sorbitol and dextran sulphate. More suitably the sugar and/or polyol is sucrose or sorbitol. More suitably the sugar and/or polyol is a sugar. More suitably the sugar is sucrose.

Suitable sugar and/or polyol concentrations in the composition of the invention may range from about 1% w/v, 3% w/v, 4% w/v, 5% w/v, 6% w/v, 7% w/v, 8% w/v, to about 10% w/v, 13% w/v, 20% w/v, 30% w/v, 35% w/v, 40% w/v, or about 70% w/v, for example from about 3% w/v to about 40% w/v, more suitably from about 4% w/v to about 35% w/v, more suitably from about 5% w/v to about 30% w/v, more suitably from about 6% w/v to about 20% w/v, more suitably from about 7% w/v to about 15% w/v, more suitably from about 8% w/v to about 13% w/v, more suitably about 10% w/v.

Suitably the concentration of the sugar and/or polyol is no more than 70% w/v, more suitably no more than 50% w/v, more suitably no more than 40% w/v, more suitably no more than 35% w/v, more suitably no more than 30% w/v, more suitably no more than 25% w/v, more suitably no more than 20% w/v, more suitably no more than 15% w/v, more suitably no more than 10% w/v.

pH

Suitably the pH of the composition is from about 5.0, 5.5, 5.7, 6.0, 6.3, 6.4 or 6.5, to about pH 6.6, 6.7, 7.0, 7.3, 7.5, or 8.0 for example between pH 5.0 and pH 8.0, more suitably between about pH 5.5 to about pH 7.5, more suitably between about pH 5.7 to about pH 7.3, more suitably between about pH 6.0 to about pH 7.0, more suitably between about pH 6.3 to about pH 6.7, more suitably between about pH 6.4 to about pH 6.6, more suitably about 6.5.

The pH of the rotavirus immunogenic composition as described herein may be obtained by mixing of adipic acid and a carboxylate salt. Alternatively, the pH of the rotavirus immunogenic composition as described herein may be obtained by mixing of adipic acid and sodium hydroxide. In particular, the adipic acid may be used in admixture with a different carboxylate salt, for example, a citrate is combined with adipic acid. This may be advantageous when using commercially available chemicals, some of which may not be readily available, or to simplify the formulation step. The skilled person will appreciate that formulation excipients may have an impact on the pH of a formulation.

Proteins/Antioxidants

Suitably the composition comprises one or more proteins or antioxidants selected from the list consisting of vitamin E succinate (VES), D-α-Tocopherol polyethylene glycol 1000 succinate (TPGS), heparin, monothioglycerol (MTG), lactalbumin, albumin and β casein. More suitably the composition comprises TPGS and/or albumin, more suitably both TPGS and albumin. Suitably the albumin is human serum albumin, more suitably recombinant human serum albumin.

Suitably albumin is present in the composition at a concentration of at least 0.05% w/v, more suitably at least 0.1% w/v, more suitably at least 0.15% w/v, more suitably at least 0.2% w/v. Suitably albumin is present in the composition at a concentration of no more than 0.2% w/v.

Suitably vitamin E succinate or TPGS is present in the composition at a concentration of at least 0.5 mM, more suitably at least 1 mM, more suitably at least 1.5 mM, more suitably at least 2 mM. Suitably vitamin E succinate or TPGS is present in the composition at a concentration of no more than 2 mM, more suitably no more than 1.5 mM, more suitably no more than 1 mM. Suitably vitamin E succinate or TPGS is present in the composition at a concentration of about or exactly 1 mM.

Other Components

The composition according to the present invention may further include a phosphate. Suitably the phosphate is selected from the group consisting of: monophosphates, polyphosphates and phosphorylated compounds. Phosphate refers as the salt of phosphoric acid (also known as orthophosphoric acid ($H_3PO_4$)), usually sodium or potassium or a mix of sodium and potassium salts are used (for example: $Na_3PO_4$, $Na_2HPO_4$, $NaH_2PO_4$, $K_3PO_4$, $K_2HPO_4$, $KH_2PO_4$). Suitably, the phosphate concentration is from about 0.05 to about 0.3 M. Typically phosphate, when present, comes from the cell culture medium or saline buffer used as a diluent, such as DMEM (Dulbecco's modified Eagle Medium), Eagle BME basal medium or phosphate-buffered saline (PBS). Suitably the phosphate is present at a concentration of from about 10 mM to about 2 M.

Suitably the composition of the invention is an aqueous solution, more suitably an aqueous saline solution.

Suitably the composition of the invention comprises a non-ionic surfactant. Suitably the non-ionic surfactant is selected from the group consisting of: polysorbates, polyoxyethylene alkyl ether, nonaethylene glycol octylphenyl ether, hepatethylene glycol octylphenyl ether, sorbitan trioleate, and polyoxyethylene-polyoxypropylene block copolymer. Suitably the non-ionic surfactant concentration is from about 0.005% w/v to about 0.1% w/v.

The composition according to the present invention may further include an additional antacid component such as an inorganic antacid, for example aluminium hydroxide $Al(OH)_3$ and/or magnesium hydroxide $Mg(OH)_2$. Aluminium hydroxide is particularly suitable. Other commercially available antacids, which are suitable for use in the invention, include MYLANTA™, which contains aluminium hydroxide and magnesium hydroxide. These are insoluble in water and are given in suspension. Another particularly suitable antacid that may be additionally used in the vaccine composition of the present invention is the insoluble inorganic salt, calcium carbonate ($CaCO_3$). A typical $CaCO_3$ concentration is 80 mg per vaccine dose for example.

Other suitable water insoluble antacids are magnesium carbonate, aluminium carbonate, aluminium phosphate, mix of aluminium hydroxide and magnesium carbonate, aluminium-magnesium-hydrycarbonate, aluminium hydroxide-magnesium carbonate-sorbitol-manitol, hydroxy-aluminium-sodium-carbonate, dihydroxy-aluminium-potassium-carbonate, magaldrate, hydrotalcite, almagcit and magnesium-aluminium-silicate-hydrate.

The composition according to the present invention may additionally comprise a pharmaceutically acceptable excipient and/or carrier, in particular those known in the art as being suitable for oral administration, especially to humans and more especially to human infants. Such carriers include carbohydrates, polyalcohols, hydroxyapatite, talc, titanium oxide, iron hydroxide, magnesium stearate, carboxymethylcellulose, hydroxypropylmethylcellulose, microcrystalline cellulose, gelatin, vegetal peptone, xanthane, caraghenane, arabic gum and β-cyclodextrin.

Suitably the composition of the invention comprises a diluent. Suitably the diluent is selected from the group consisting of: a tissue culture medium, saline, phosphate-buffered saline and water.

Viscous agents may additionally be included in the composition. Viscous agents that may be used include pseudoplastic excipients. Suitable viscous agents include: propylene glycol, arabic gum, adragant gum, agar-agar, alginate, pectin, sodium carboxymethylcellulose (TYLOSES C™), methylcellulose (METHOCELS A™, VISCOTRANS MC™, TYLOSE MH™ and MB™), hydroxypropylmethylcellulose (KLUCELS™), hydroxypropylcellulose (METHOCELS E™ and K™, VICOTRANS MPHC™), CARBOPOL™, xanthane gum, VEEGUM™ (Magnesium-aluminium silicate), AVICEL™ (about 89% microcrystalline cellulose and 11% Carboxymethylcellulose Na). Xanthane gum or starch are particularly suitable viscous agents for use in the composition according to the invention.

It may also be advantageous to include in the compositions of the present invention lipid-based vehicles such as virosomes or liposomes, oil-in-water emulsions or carrier particles. Alternatively or in addition immunostimulants such as those known in the art for oral vaccines may be included in the composition. Such immunostimulants include bacterial toxins, particularly cholera toxin (CT) in the form of the holotoxin (entire molecule) or the B chain only (CTB) and the heat labile enterotoxin of E. coli (LT). Mutated LTs (mLTs) which are less likely to convert to their active form than the native LT are described in WO 96/06627, WO 93/13202 and U.S. Pat. No. 5,182,109.

The composition according to the invention may further comprise an adjuvant or immunostimulant such as but not limited to detoxified lipid A from any source and non-toxic derivatives of lipid A, saponins and other reagents capable of stimulating a TH1 type response.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., N.Y., p407-419).

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

A suitable form of 3D-MPL is in the form of an emulsion having a small particle size less than 0.2 μm in diameter, and its method of manufacture is disclosed in WO 94/21292. Aqueous compositions comprising monophosphoryl lipid A and a surfactant have been described in WO9843670A2.

The bacterial lipopolysaccharide derived adjuvants to be formulated in the compositions of the present invention may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella sp.* is described in GB 2220211 and U.S. Pat. No. 4,912,094. Other purified and synthetic lipopolysaccharides have been described (Hilgers et al., 1986, *Int.Arch.Allergy.Immunol.*, 79(4):392-6; Hilgers et al., 1987, *Immunology*, 60(1):141-6; and EP 0 549 074 B1). A particularly suitable bacterial lipopolysaccharide adjuvant is 3D-MPL.

Accordingly, the LPS derivatives that may be used in the present invention are those immunostimulants that are similar in structure to that of LPS or MPL or 3D-MPL. In another aspect of the present invention the LPS derivatives may be an acylated monosaccharide, which is a sub-portion to the above structure of MPL.

Synthetic derivatives of lipid A are also known including, but not limited to:

OM 174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S, 9 R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-, 9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127)

Purified saponins as oral adjuvants are described in WO 98/56415. Saponins and monophosphoryl lipid A may be employed separately or in combination (e.g. as described in WO 94/00153) and may be formulated in adjuvant systems together with other agents. 3D-MPL is a well-known adjuvant manufactured by Corixa Corporation, Montana and its manufacture is described in GB 2122204.

Another prefered immunostimulant for use in the present invention is Quil A saponin and its derivatives. Saponins are taught in: Lacaille-Dubois, M and Wagner H. (1996. A review of the biological and pharmacological activities of saponins. *Phytomedicine* vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., *Crit Rev Ther Drug Carrier Syst*, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. QS-21 is a natural saponin derived from the bark of *Quillaja saponaria Molina*, which induces CD8+ cytotoxic T cells (CTLs), Th1 cells and a predominant IgG2a antibody response and is a suitable saponin in the context of the present invention. Other saponins which have been used in systemic vaccination studies include those derived from other plant species such as Gypsophila and Saponaria (Bomford et al., *Vaccine*, 10(9):572-577, 1992).

An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739. The saponins may be separate in the form of micelles, or may be in the form of large ordered structures (such as ISCOMs (EP 0 109 942 B1) or liposomes) when formulated with cholesterol and lipid, or in the form of an oil-in-water emulsion (WO 95/17210). The saponins may suitably be associated with a metallic salt, such as aluminium hydroxide or aluminium phosphate (WO 98/15287).

Potent adjuvant compositions comprising QS21 and 3D-MPL in an oil-in-water emulsion are described in WO 95/17210 and in WO 99/11241 and WO 99/12565, and are suitable compositions.

A general discussion of vehicles and adjuvants for oral immunisation can be found in Vaccine Design, The Subunit and Adjuvant Approach, edited by Powell and Newman, Plenum Press, N.Y., 1995.

The vaccine composition according to the invention may contain additional components including for example flavourings (particularly for an oral vaccine) and bacteriostatic agents.

Additional Antigens

The composition of the invention may also be formulated to contain further, additional antigens, in particular antigens from other suitable viruses for protection against other diseases, for example poliovirus. Said additional antigens may be given either in admixture with the rotavirus composition, or alternatively may be co-administered (i.e. in a separate dose but on the same occasion) with the rotavirus compositions of the present invention.

The compositions of the present invention may also be given concomitantly with other (for example, non-oral) vaccines, for example with parenteral vaccines suitable for the paediatric vaccinee population such as DTPw or DTPa vaccines (vaccines against Bordetella pertussis—whooping cough, diphteria, tetanus), vaccines against Haemophilus influenza B-induced meningitis, hepatitis B, or measles, mumps, rubella (MMR), vaccines against Streptococcus pneumoniae, in order to reduce the number of visits to the doctor.

Particular Formulations

Suitably the composition according to the invention comprises the following:

a virus, such as a rotavirus, at a titre ranging from about $1 \times 10^5$ to about $1 \times 10^8$ pfu/mL,
sucrose at a concentration of 5% w/v to 35% w/v,
adipate buffer at a concentration of 3% to about 10% w/v,
calcium ions at a concentration of 3 mM to about 7 mM,
histidine at a concentration of at least 0.05% w/v.

Alternatively, the composition of the invention may comprise the following:

a virus, such as a rotavirus, at a titre ranging from about $1 \times 10^5$ to about $1 \times 10^8$ pfu/mL,
sucrose at a concentration of 5% w/v to 35% w/v,
adipate buffer at a concentration of 3% to about 10% w/v,
calcium ions at a concentration of 3 mM to about 7 mM,
arginine at a concentration of at least 0.05% w/v.

Thermostability

The thermostability of a viral composition, such as a rotavirus composition may be assessed by measuring the virus titer of the composition, then storing the composition at a set temperature for a set period of time, followed by measuring the virus titer loss relative to the virus titer before storage, expressed in $\log_{10}$ ffu/mL. Thus, as used herein, stability of a virus or a viral formulation refers to the ability to resist or slow decreases in viral titer over time; thermostability refers to the ability to resist or slow decreases in viral titer due to heat (e.g., storage at non-refrigerated temperatures).

Suitably the composition of the invention has a level of thermostability such that, after storage of the composition for 2.5 months at 37° C., the composition has a maximum virus titer loss of 1.5, more suitably 1.4, more suitably 1.3, more suitably 1.2; as expressed in $\log_{10}$ ffu/mL (loss as compared to the composition's initial rotavirus titer, before storage).

Suitably the composition of the invention has a level of thermostability such that, after storage of the composition for seven weeks at 40° C., the composition has a maximum rotavirus titer loss of 2.0, more suitably 1.5, more suitably 1.4, more suitably 1.3, more suitably 1.2; as expressed in $\log_{10}$ ffu/mL (loss as compared to the composition's initial rotavirus titer, before storage).

A suitable method for measuring $\log_{10}$ ffu/mL is as follows. Sample dilutions are inoculated on a MA-104 lawn cell for 16-18 hours at 37° C.±1° C. to allow for a viral replication cycle. Viral particles are revealed by immunoluminescence. After incubation, viral particles are detected by monoclonal (9F6) antibody (against VP6) which is further revealed by a second antibody (anti-mouse) coupled with HRP. Trublue reagent is then added and turned into blue dots. Rotavirus identity is confirmed by using highly specific 9F6 monoclonal antibody against VP6. The viral titre is obtained by counting the blue dots and may be expressed in FFU/ml or FFU/dose.

A suitable method for measuring $CCID_{50}$ is as follows. Sample dilutions are inoculated on a MA-104 lawn cell for 7 days±1 day at 37° C.±1° C. Viral particles are detected by immunofluorescence method. After incubation, infected cells come into contact with anti-rotavirus 2C9 monoclonal antibody (against VP7) which is further revealed by a second antibody (anti-mouse) coupled with fluorescence molecule (FITC=Fluorescein IsoThioCyanate). Observation of fluorescent cells under the microscope indicates that the cell lawn was well infected by the rotavirus. Rotavirus identity is confirmed by using highly specific 2C9 monoclonal antibody against VP7. The viral titre is obtained by the Reed and Muench calculation method (Reed and Muench (1938) *The American Journal of Hygiene* 27:493-497) and may be expressed in $CCID_{50}$/ml or $CCID_{50}$/dose.

Administration

The terms 'formulation' and 'composition' are used interchangeably herein. Suitably the formulation of the invention is a vaccine. The formulation may be provided in the form of a liquid formulation (such as a liquid suspension) or a dry formulation (such as a powder, a dissolving tablet for dissolution when placed in the mouth, or an oral thin film).

Suitably the composition according to the invention is administered by oral administration, suitably to humans and more suitably to human infants. Suitably the composition is supplied in a single-dose device, such as a glass or plastic vial or syringe, suitable for delivery to infants.

The composition according to the present invention is an immunogenic composition, e.g. it is suitably a vaccine. As used herein, a vaccine refers to an immunogenic composition capable, after a suitable dosing regime in a subject, of eliciting an immune response in that subject specific to an antigen contained in the vaccine. A vaccine will reduce the occurrence or incidence of infection and/or disease (specific to the vaccine's target pathogen) in an appropriately treated population.

As used herein, a rotavirus vaccine is an immunogenic composition capable, typically after one, suitably two doses separated by one or two months, of eliciting an immune response to rotaviral antigen(s) contained in the vaccine, e.g. a serum rotavirus specific IgA response. As used herein a vaccine also demonstrates an acceptable 'vaccine take,' defined as the percentage of subjects displaying either a serological response, e.g. appearance of serum IgA to rotavirus in post-immunization sera at a titer ≥20 U/ml (ELISA), and/or with rotavirus shedding (ELISA) in any stool sample. Vaccine take can be defined as vaccine virus shedding in any stool sample collected between the first dose and up to 1 to 2 months after the second dose.

In one aspect of the invention there is provided the use of the immunogenic composition of the invention in the manufacture of a medicament for use in the treatment or prevention of viral infection. In one aspect of the invention the immunogenic composition is a rotavirus vaccine administered to humans, including human infants, and the infection is a rotavirus infection that affects humans.

In a further aspect of the invention there is provided a method for the prevention of rotavirus infection, and/or rotavirus-associated disease such as gastroenteritis and/or diarrhea, in humans, including human infants, where the method comprises administering a rotavirus vaccine composition of the invention to a subject at risk of rotavirus infection.

In a specific embodiment, the rotavirus vaccine according to the invention is capable of decreasing the risk of, or the occurrence of any, and preferably severe, rotavirus gastroenteritis as compared to placebo. Typically the vaccine is able to confer cross-protection against circulating strains of rotavirus other than that present in the vaccine. Typically, when the vaccine contains a G1 type strain such as that of the attenuated human virus P43, an immune response is induced to G1 and at least one of the non-G1 serotypes selected from the group consisting of: G2, G3, G4, G5, G6, G7, G8, G9, G10, G11, G12, G13 and G14 serotypes. Suitably a vaccine containing a G1 strain is capable of conferring protection against both G1 and non-G1 strains, such as G2, G3 and/or G4 strains, and in particular against the globally emerging G9 serotype.

In a specific embodiment, the rotavirus infection causes gastroenteritis or severe gastroenteritis. In one embodiment, the gastroenteritis or severe gastroenteritis is caused by a rotavirus strain of the same serotype to that contained in the rotavirus vaccine composition of the invention.

In a further embodiment, the gastroenteritis or severe gastroenteritis is caused by a rotavirus strain of a different serotype to that contained in the rotavirus vaccine composition of the invention. In particular, if the rotavirus strain present in the composition is a G1 serotype, such as but not limited to the live attenuated human rotavirus strain HRV P43 (ECACC 99081301), prevention is conferred against gastroenteritis or severe gastroenteritis caused by a rotavirus strain of a G1 serotype and also by a rotavirus strain of a non-G1 serotype, for example by a rotavirus strain having a serotype selected from the list consisting of: G2, G3, G4, G5, G6, G7, G8, G9, G10, G11, G12, G13 and G14. In a particular embodiment, the immunogenic composition is capable of inducing an immune response against, and/or provide protection against gastroenteritis or severe gastroenteritis caused by, at least one, suitably all of the following non-G1 serotypes: G2, G3, G4 and G9. In another specific embodiment, if the rotavirus strain present in the composition of the present invention is a P[8] rotavirus type, such as but not limited to the live attenuated human rotavirus strain HRV P43 (ECACC 99081301), prevention is conferred against gastroenteritis or severe gastroenteritis caused by a rotavirus strain of a P[8] type and by a non- P[8] type, for example by a rotavirus strain having a serotype selected from the list consisting of: P1, P2, P3, P4, P5, P6, P7, P9 and P11 types. In particular, the immunogenic composition described herein is capable of inducing an immune response against, and/or provide protection against gastroenteritis or severe gastroenteritis caused by, at least one, suitably all of the following non- P[8] type: P4, P6. In another embodiment, the composition is capable of inducing an immune response to, and/or provide protection against gastroenteritis or severe gastroenteritis caused by, a rotavirus strain of a different G type and a different P type to that present in the administered composition. Suitably the composition is also capable of inducing an immune response to, and/or provide protection against gastroenteritis or severe gastroenteritis caused by, a G2P[4] rotavirus strain.

The immunogenic composition of the invention is suitably provided in a form suitable for oral delivery.

In one embodiment, a vaccine according to the present invention is administered as a liquid formulation. Suitably the liquid formulation is reconstituted prior to administration from at least the following two components:

i) virus component;
ii) liquid diluent component.

In this embodiment, the virus component and the liquid diluent component are normally present in separate containers, which may conveniently be separate compartments of a single vessel, or separate vessels which can be connected in such a way that the final vaccine composition is reconstituted without exposing it to the air.

Prior to reconstitution, the virus may be in a dry form or a liquid form. Suitably, in a rotavirus vaccine, the rotavirus is lyophilised. Lyophilised virus is more stable than virus in an aqueous solution. The lyophilised virus may be suitably reconstituted using a liquid antacid composition to produce a liquid formulation. Alternatively the lyophilised virus may be reconstituted with water or aqueous solution, in which case the lyophilised virus composition suitably contains an antacid component.

In another embodiment, the immunogenic composition or vaccine of the invention is a solid formulation, such as a lyophilised composition, suitably a lyophilised cake which is suitable for immediate dissolution when placed in the mouth. Lyophilised formulations may conveniently be provided in the form of tablets. In another aspect the invention provides a vaccine, such as a rotavirus vaccine, in the form of a quick dissolving tablet for oral administration.

The composition according to the invention may be provided in the form of an oral thin film. Accordingly, an oral thin film ("OTF", also known as a "dissolving film" or "oral drug strip") may be used to administer the immunogenic composition of the invention via absorption in the mouth (buccally or sublingually). Preferably, an OTF comprising an immunogenic composition of the invention is for buccal or sublingual administration. An OTF may be prepared, for example, by using hydrophilic polymers that rapidly dissolve on the tongue or buccal cavity, delivering the immunogenic composition to the systemic circulation via dissolution when contact with liquid is made. According to one aspect of the invention there is provided an OTF comprising an immunogenic composition of the invention.

A suitable amount of virus will normally be between $10^4$ and $10^7$ ffu per vaccine dose. A typical dose of vaccine may comprise $10^5$-$10^6$ffu per dose, and multiple doses may be given over a period of time, for example two doses given at a two-month interval. Rotavirus titer may also be expressed in $CCID_{50}$ and it can be estimated in the context of this invention that a $CCID_{50}$ of $10^{6.0}$ is equivalent to a ffu of $10^{5.5}$ per dose. Benefits may however be obtained by having more than 2 doses, for example a 3 or 4 dose regimen, particularly in developing countries. The first dose can suitably be given to infants at from about 4 weeks to about 14 or 15 weeks of age, suitably between 6 and 14 weeks of age. The interval between doses is at least 4 weeks but may be more or less than two months long, for example the second dose, and any subsequent dose if appropriate, may be given one month or three months after the previous dose, depending on the local immunisation schedule. An optimal amount of virus for a single dose or for a multiple dose regimen, and optimal timing for the doses, can be ascertained by standard studies involving observation of antibody titers and other responses in subjects.

Typically the volume of a dose of vaccine according to the invention will be 2.5 ml or lower, typically 0.2 ml to 2.0 ml. In a specific aspect of the invention, a suitable dose will normally be 1.5 ml or suitably any volume smaller than 2.5 ml such as a volume of 2 ml or less, that is suitable for oral administration to babies or infants. In particular the dose volume will be such that the technical feasibility of the formulation is possible and there is no detrimental effect on the immunogenic potential of the formulation. Suitably the dose volume is 0.5 ml to 1.5 ml, suitably approximately 1.0 ml to 1.5 ml, such as about 1.3 ml or about 1.4 ml or about 1.5 ml.

In one aspect there is provided a kit comprising the immunogenic composition according to the invention and instructions for use of the kit.

The subject matter of and information disclosed within the publications and patents or patent applications mentioned in this specification are incorporated by reference in their entirety herein.

The present invention will now be further described by means of the following non-limiting examples.

EXAMPLES

In all examples, the rotavirus concentration was 6.3 $\log_{10}$ CCID/ml.

Example 1: Effect of Different Carboxylates, Different Divalent Cations and Different Sugars/Polyols on the Thermostability of Rotavirus Formulations The effects of the following components on the thermostability of liquid rotavirus formulations were assessed:
Buffers: adipic acid, citric acid.
Divalent cation: no divalent cation, calcium chloride, magnesium sulphate, zinc chloride, Sugar or Polyol: sucrose, glucose, maltose, trehalose dihydrate, fructose, α-cyclodextrin, sorbitol, dextran sulfate.

Table 1 below provides details on each tested composition. Each tested composition had a volume of 1.4 ml and at a pH of 6.5. 'Ch' refers to chloride.

TABLE 1

| Run | Buffer | Conc. (w/v) | Sugar/ Polyol | Conc. (w/v) | Divalent cation | Conc. (mM) |
| --- | --- | --- | --- | --- | --- | --- |
| 1 | Citric acid | 3.13% | Sorbitol | 30% | Calcium Ch | 15 mM |
| 2 | Citric acid | 3.13% | Sorbitol | 30% | Zinc Ch | 15 mM |
| 3 | Citric acid | 3.13% | Maltose | 9% | No divalent | |
| 4 | Citric acid | 3.13% | Glucose | 30% | Zinc Ch | 15 mM |
| 5 | Citric acid | 3.13% | Cyclodextrin | 6% | Zinc Ch | 15 mM |
| 6 | Adipic acid | 6.70% | Glucose | 30% | Magnesium | 15 mM |
| 7 | Citric acid | 3.13% | Sucrose | 30% | Magnesium | 15 mM |
| 8 | Citric acid | 3.13% | Dextran | 4.80% | No divalent | |
| 9 | Citric acid | 3.13% | Cyclodextrin | 6% | Magnesium | 15 mM |
| 10 | Citric acid | 3.13% | Cyclodextrin | 6% | Calcium Ch | 15 mM |
| 11 | Adipic acid | 6.70% | Sucrose | 30% | Zinc Ch | 15 mM |
| 12 | Citric acid | 3.13% | Maltose | 9% | Zinc Ch | 15 mM |
| 13 | Citric acid | 3.13% | Glucose | 30% | Calcium Ch | 15 mM |
| 14 | Adipic acid | 6.70% | Trehalose | 30% | No divalent | |
| 15 | Adipic acid | 6.70% | Cyclodextrin | 6% | Calcium Ch | 15 mM |
| 16 | Adipic acid | 6.70% | Dextran | 4.80% | Magnesium | 15 mM |
| 17 | Adipic acid | 6.70% | Maltose | 9% | Zinc Ch | 15 mM |
| 18 | Citric acid | 3.13% | Sorbitol | 30% | No divalent | |
| 19 | Citric acid | 3.13% | Glucose | 30% | No divalent | |
| 20 | Citric acid | 3.13% | Fructose | 30% | No divalent | |
| 21 | Citric acid | 3.13% | Fructose | 30% | Magnesium | 15 mM |
| 22 | Adipic acid | 6.70% | Maltose | 9% | Calcium Ch | 15 mM |
| 23 | Citric acid | 3.13% | Maltose | 9% | Calcium Ch | 15 mM |
| 24 | Adipic acid | 6.70% | Sorbitol | 30% | Calcium Ch | 15 mM |
| 25 | Adipic acid | 6.70% | Sucrose | 30% | Magnesium | 15 mM |
| 26 | Adipic acid | 6.70% | Fructose | 30% | No divalent | |
| 27 | Adipic acid | 6.70% | Sucrose | 30% | No divalent | |
| 28 | Adipic acid | 6.70% | Cyclodextrin | 6% | Magnesium | 15 mM |
| 29 | Citric acid | 3.13% | Glucose | 30% | Magnesium | 15 mM |
| 30 | Citric acid | 3.13% | Sucrose | 30% | Zinc Ch | 15 mM |
| 31 | Citric acid | 3.13% | Cyclodextrin | 6% | No divalent | |
| 32 | Adipic acid | 6.70% | Sorbitol | 30% | Magnesium | 15 mM |
| 33 | Adipic acid | 6.70% | Sorbitol | 30% | No divalent | |
| 34 | Adipic acid | 6.70% | Glucose | 30% | No divalent | |
| 35 | Citric acid | 3.13% | Sorbitol | 30% | Magnesium | 15 mM |
| 36 | Adipic acid | 6.70% | Dextran | 4.80% | No divalent | |
| 37 | Adipic acid | 6.70% | Cyclodextrin | 6% | No divalent | |
| 38 | Adipic acid | 6.70% | Fructose | 30% | Magnesium | 15 mM |
| 39 | Citric acid | 3.13% | Maltose | 9% | Magnesium | 15 mM |
| 40 | Adipic acid | 6.70% | Fructose | 30% | Calcium Ch | 15 mM |
| 41 | Adipic acid | 6.70% | Maltose | 9% | No divalent | |
| 42 | Citric acid | 3.13% | Trehalose | 30% | Zinc Ch | 15 mM |
| 43 | Adipic acid | 6.70% | Dextran | 4.80% | Calcium Ch | 15 mM |
| 44 | Citric acid | 3.13% | Dextran | 4.80% | Calcium Ch | 15 mM |
| 45 | Citric acid | 3.13% | Dextran | 4.80% | Magnesium | 15 mM |
| 46 | Citric acid | 3.13% | Trehalose | 30% | No divalent | |
| 47 | Adipic acid | 6.70% | Trehalose | 30% | Magnesium | 15 mM |
| 48 | Citric acid | 3.13% | Trehalose | 30% | Magnesium | 15 mM |
| 49 | Adipic acid | 6.70% | Trehalose | 30% | Calcium Ch | 15 mM |
| 50 | Citric acid | 3.13% | Sucrose | 30% | Calcium Ch | 15 mM |
| 51 | Citric acid | 3.13% | Sucrose | 30% | No divalent | |
| 52 | Adipic acid | 6.70% | Cyclodextrin | 6% | Zinc Ch | 15 mM |
| 53 | Citric acid | 3.13% | Dextran | 4.80% | Zinc Ch | 15 mM |
| 54 | Adipic acid | 6.70% | Glucose | 30% | Calcium Ch | 15 mM |
| 55 | Adipic acid | 6.70% | Maltose | 9% | Magnesium | 15 mM |
| 56 | Control Rota | 6.70% | Sucrose | 72% | No divalent | |
| 57 | Citric acid | 3.13% | Fructose | 30% | Calcium Ch | 15 mM |
| 58 | Citric acid | 3.13% | Fructose | 30% | Zinc Ch | 15 mM |
| 59 | Adipic acid | 6.70% | Sucrose | 30% | Calcium Ch | 15 mM |
| 60 | Citric acid | 3.13% | Trehalose | 30% | Calcium Ch | 15 mM |

Six replicates of each formulation were tested. The thermostability of each formulation was assessed by measuring log FFU/ml of rotavirus after storage for 7 days at 45° C.

Out of the 59 non-control compositions, 14 compositions provided LOG ffu/ml readings above limit of quantification (LOQ). The results of these tests are shown in FIG. 1. Each replicate of a formulation is shown with a different symbol (some data points are obscured by other data points). REF refers to a reference sample of bench-prepared ROTARIX™ oral rotavirus vaccine (run 27 in Table 1 above). The REF composition differs from commercially-available ROTARIX™ in that the REF composition contains 30% w/v sucrose (as opposed to 72% sucrose) and has a pH of 6.5 (as opposed to a pH of 7). 'Control Rota' and 'Control Ro' refer to a control composition comprising 72% w/v sucrose, 6.7% w/v adipic acid and having a pH of 6.5.

Only the seven circled test formulations demonstrated a LOG ffu/ml above LOQ for all repeats. It can be seen from FIG. 1 that formulations incorporating maltose, trehalose and α-cyclodextrin provided relatively poor or inconsistent rotavirus thermostability.

Figure 2:
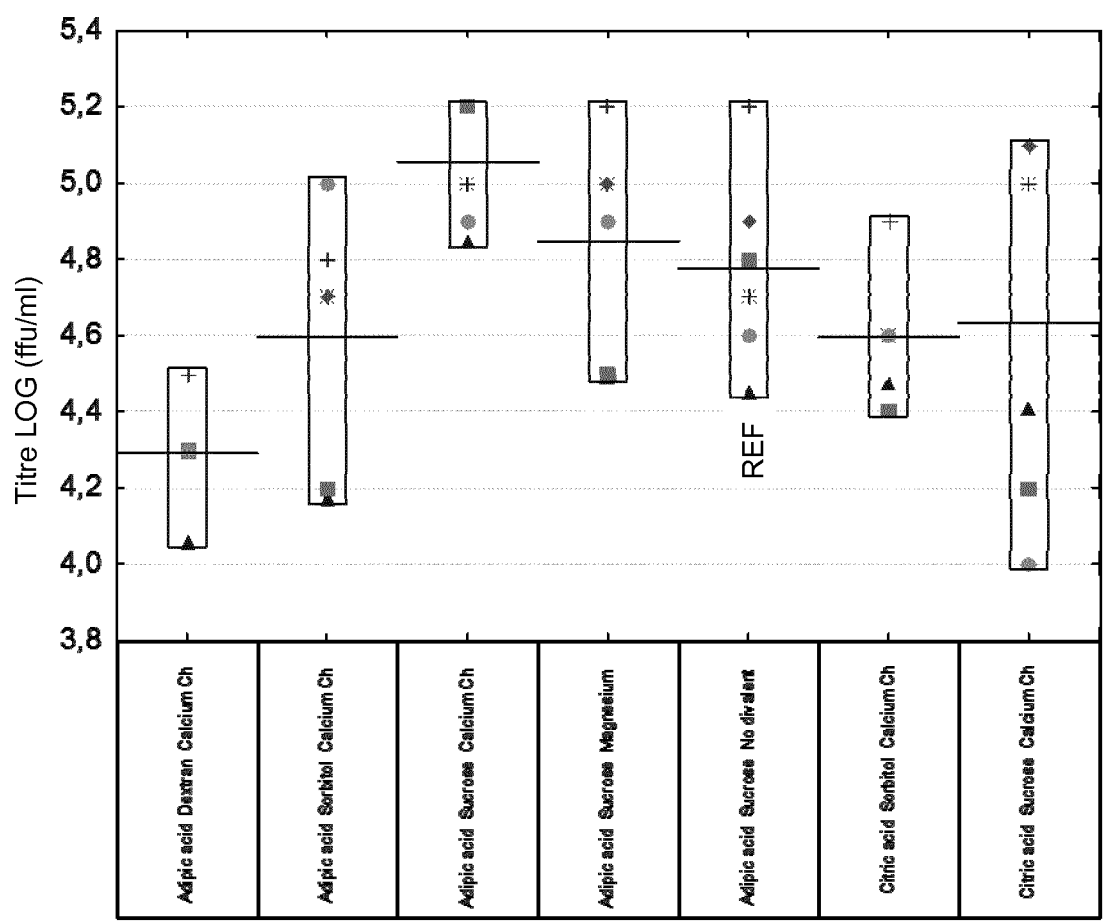
FIG. 2—Thermostability impact of different buffers, divalent cations and sugars/polyols (subset of data from FIG. 1)

These seven highlighted formulations are also shown for further comparison in FIG. 2. It can be seen from FIG. 2 that the formulation comprising adipic acid, sucrose and calcium had the highest average LOG ffu/ml (indicated by horizontal lines on FIG. 2) and the formulation comprising adipic acid, sucrose and magnesium had the second highest average LOG ffu/ml. Both of these formulations had a higher average LOG ffu/ml than the reference formulation (which comprised no divalent cation). The formulations comprising dextran or sorbitol, as opposed to sucrose, had average LOG ffu/ml readings which were lower than the reference. The formulations comprising citric acid, as opposed to adipic acid, had average LOG ffu/ml readings lower than the reference.

Example 2: Effect of Particular Amino Acids on the Thermostability of Rotavirus Formulations The effect of adding particular amino acids (and calcium pantothenate) to rotavirus formulations comprising (a) sucrose, adipic acid and calcium or (b) sucrose, adipic acid and magnesium was assessed.

Table 2 below provides details on each tested composition. Each tested composition had a volume of 1.4 ml and at a pH of 6.5. 'Ch' refers to chloride. 'CTRL' refers to no amino acid present.

TABLE 2

| Run | Buffer Type | Conc. (w/v) | Polyol | Conc. (w/v) | Divalent cation | Conc. | Amino acid | Conc. (w/v) |
|---|---|---|---|---|---|---|---|---|
| 1 | Adipic acid | 6.70% | Sucrose | 30% | Magnesium | 15 mM | CTRL | — |
| 2 | Adipic acid | 6.70% | Sucrose | 30% | Magnesium | 15 mM | Aspartic acid | 0.028% |
| 3 | Adipic acid | 6.70% | Sucrose | 30% | Magnesium | 15 mM | Proline | 0.1% |
| 4 | Adipic acid | 6.70% | Sucrose | 30% | Magnesium | 15 mM | Threonine | 0.1% |
| 5 | Adipic acid | 6.70% | Sucrose | 30% | Magnesium | 15 mM | Valine | 0.1% |
| 6 | Adipic acid | 6.70% | Sucrose | 30% | Magnesium | 15 mM | Histidine | 0.1% |
| 7 | Adipic acid | 6.70% | Sucrose | 30% | Magnesium | 15 mM | Methionine | 0.1% |
| 8 | Adipic acid | 6.70% | Sucrose | 30% | Magnesium | 15 mM | Arginine | 0.1% |
| 9 | Adipic acid | 6.70% | Sucrose | 30% | Magnesium | 15 mM | Tyrosine | 0.0014% |
| 10 | Adipic acid | 6.70% | Sucrose | 30% | Magnesium | 15 mM | Calcium pantothénate | 0.1% |
| 11 | Adipic acid | 6.70% | Sucrose | 30% | Magnesium | 15 mM | Cysteine | 0.1% |
| 12 | Adipic acid | 6.70% | Sucrose | 30% | Magnesium | 15 mM | Sodium glutamate | 0.1% |
| 13 | Adipic acid | 6.70% | Sucrose | 30% | Magnesium | 15 mM | Glycine | 0.1% |
| 14 | Adipic acid | 6.70% | Sucrose | 30% | No divalent | — | CTRL | — |
| 15 | Adipic acid | 6.70% | Sucrose | 30% | No divalent | — | Aspartic acid | 0.028% |
| 16 | Adipic acid | 6.70% | Sucrose | 30% | No divalent | — | Proline | 0.1% |
| 17 | Adipic acid | 6.70% | Sucrose | 30% | No divalent | — | Threonine | 0.1% |
| 18 | Adipic acid | 6.70% | Sucrose | 30% | No divalent | — | Valine | 0.1% |
| 19 | Adipic acid | 6.70% | Sucrose | 30% | No divalent | — | Histidine | 0.1% |
| 20 | Adipic acid | 6.70% | Sucrose | 30% | No divalent | — | Methionine | 0.1% |
| 21 | Adipic acid | 6.70% | Sucrose | 30% | No divalent | — | Arginine | 0.1% |
| 22 | Adipic acid | 6.70% | Sucrose | 30% | No divalent | — | Tyrosine | 0.0014% |
| 23 | Adipic acid | 6.70% | Sucrose | 30% | No divalent | — | Calcium pantothénate | 0.1% |
| 24 | Adipic acid | 6.70% | Sucrose | 30% | No divalent | — | Cysteine | 0.1% |
| 25 | Adipic acid | 6.70% | Sucrose | 30% | No divalent | — | Sodium glutamate | 0.1% |
| 26 | Adipic acid | 6.70% | Sucrose | 30% | No divalent | — | Glycine | 0.1% |

TABLE 2-continued

| Run | Buffer Type | Conc. (w/v) | Polyol | Conc. (w/v) | Divalent cation | Conc. | Amino acid | Conc. (w/v) |
|---|---|---|---|---|---|---|---|---|
| 27 | Citric acid | 3.13% | Sucrose | 30% | Calcium Ch | 15 mM | CTRL | — |
| 28 | Citric acid | 3.13% | Sucrose | 30% | Calcium Ch | 15 mM | Aspartic acid | 0.028% |
| 29 | Citric acid | 3.13% | Sucrose | 30% | Calcium Ch | 15 mM | Proline | 0.1% |
| 30 | Citric acid | 3.13% | Sucrose | 30% | Calcium Ch | 15 mM | Threonine | 0.1% |
| 31 | Citric acid | 3.13% | Sucrose | 30% | Calcium Ch | 15 mM | Valine | 0.1% |
| 32 | Citric acid | 3.13% | Sucrose | 30% | Calcium Ch | 15 mM | Histidine | 0.1% |
| 33 | Citric acid | 3.13% | Sucrose | 30% | Calcium Ch | 15 mM | Methionine | 0.1% |
| 34 | Citric acid | 3.13% | Sucrose | 30% | Calcium Ch | 15 mM | Arginine | 0.1% |
| 35 | Citric acid | 3.13% | Sucrose | 30% | Calcium Ch | 15 mM | Tyrosine | 0.0014% |
| 36 | Citric acid | 3.13% | Sucrose | 30% | Calcium Ch | 15 mM | Calcium pantothénate | 0.1% |
| 37 | Citric acid | 3.13% | Sucrose | 30% | Calcium Ch | 15 mM | Cysteine | 0.1% |
| 38 | Citric acid | 3.13% | Sucrose | 30% | Calcium Ch | 15 mM | Sodium glutamate | 0.1% |
| 39 | Citric acid | 3.13% | Sucrose | 30% | Calcium Ch | 15 mM | Glycine | 0.1% |
| 40 | Adipic acid | 6.70% | Sucrose | 30% | Calcium Ch | 15 mM | CTRL | — |
| 41 | Adipic acid | 6.70% | Sucrose | 30% | Calcium Ch | 15 mM | Aspartic acid | 0.028% |
| 42 | Adipic acid | 6.70% | Sucrose | 30% | Calcium Ch | 15 mM | Proline | 0.1% |
| 43 | Adipic acid | 6.70% | Sucrose | 30% | Calcium Ch | 15 mM | Threonine | 0.1% |
| 44 | Adipic acid | 6.70% | Sucrose | 30% | Calcium Ch | 15 mM | Valine | 0.1% |
| 45 | Adipic acid | 6.70% | Sucrose | 30% | Calcium Ch | 15 mM | Histidine | 0.1% |
| 46 | Adipic acid | 6.70% | Sucrose | 30% | Calcium Ch | 15 mM | Methionine | 0.1% |
| 47 | Adipic acid | 6.70% | Sucrose | 30% | Calcium Ch | 15 mM | Arginine | 0.1% |
| 48 | Adipic acid | 6.70% | Sucrose | 30% | Calcium Ch | 15 mM | Tyrosine | 0.0014% |
| 49 | Adipic acid | 6.70% | Sucrose | 30% | Calcium Ch | 15 mM | Calcium pantothénate | 0.1% |
| 50 | Adipic acid | 6.70% | Sucrose | 30% | Calcium Ch | 15 mM | Cysteine | 0.1% |
| 51 | Adipic acid | 6.70% | Sucrose | 30% | Calcium Ch | 15 mM | Sodium glutamate | 0.1% |
| 52 | Adipic acid | 6.70% | Sucrose | 30% | Calcium Ch | 15 mM | Glycine | 0.1% |

Six replicates of each formulation were tested: three replicates in a first analytical run and three replicates in a second analytical run. The thermostability of each formulation was assessed by measuring LOG ffu/ml of rotavirus after storage for 10 days at 45° C.

The average LOG ffu/ml for all formulations containing adipic acid and no divalent cation was lower than the average LOG ffu/ml for all formulations containing adipic acid and magnesium or calcium. The average LOG ffu/ml for all formulations containing citric acid and calcium was lower still (data not shown).

Calcium Ion- and Adipic Acid-Containing Formulations

Figure 3:
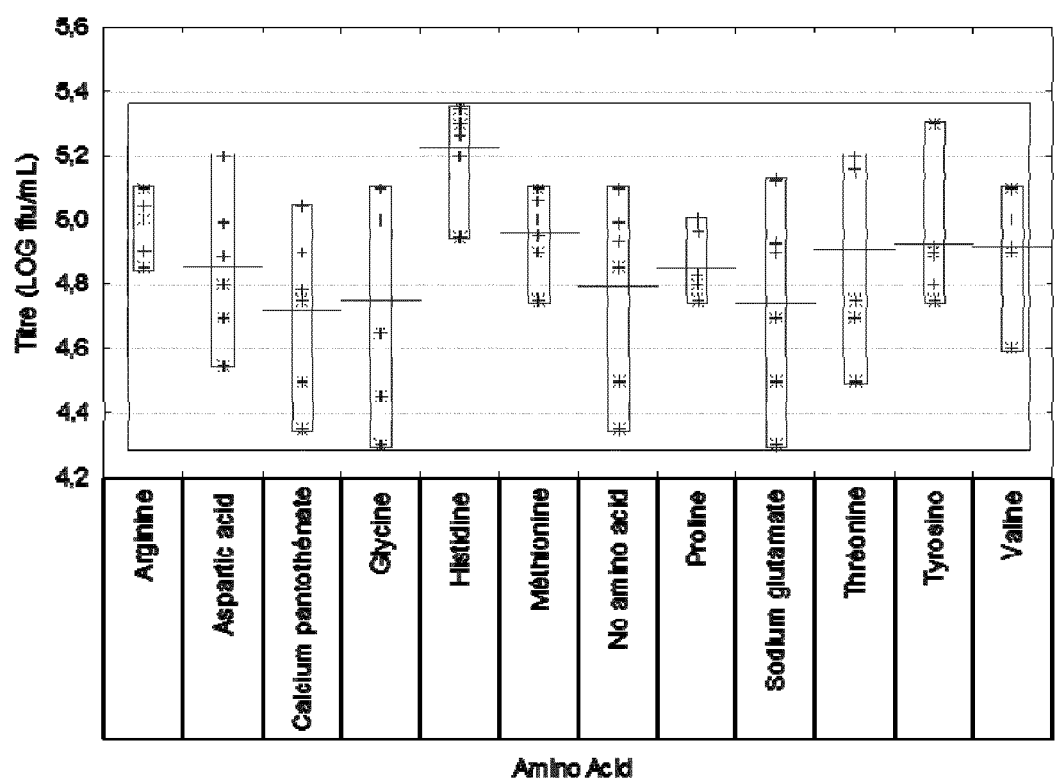
FIG. 3—Thermostability impact of different amino acids on calcium ion-containing formulations after 10 days at 45° C.

The results of the assessment in respect of adipic acid and calcium ion-containing formulations are shown in FIG. 3. Data from the first analytical run is denoted by the + symbol and data from the second analytical run is denoted by the * symbol. It can be seen from this figure that the tested amino acids provide varying levels of rotavirus thermostability enhancement. In the context of these formulations comprising calcium ions, histidine provided a particularly high average level of thermostability enhancement, followed by arginine.

Magnesium Ion- and Adipic Acid-Containing Formulations

Figure 4:
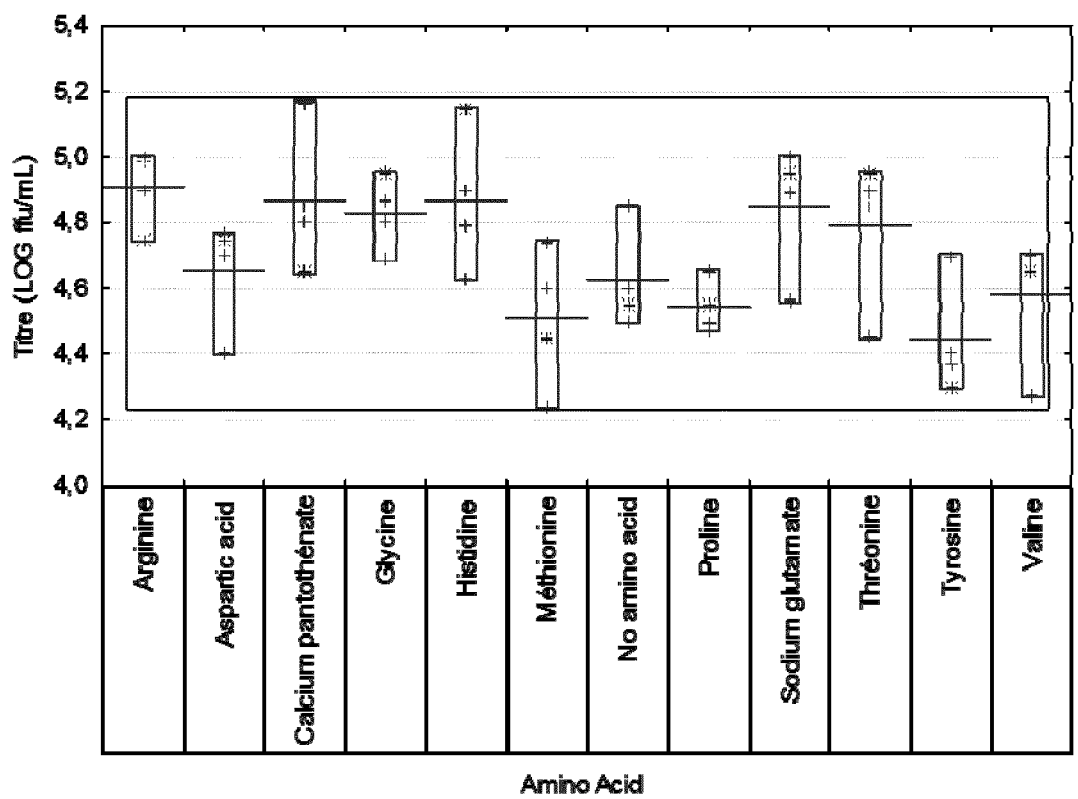
FIG. 4—Thermostability impact of different amino acids on magnesium ion-containing formulations after 10 days at 45° C.

The results of the assessment in respect of adipic acid and magnesium ion-containing formulations are shown in FIG. 4. Data from the first analytical run is denoted by the + symbol and data from the second analytical run is denoted by the * symbol. It can be seen from this figure that the tested amino acids provide varying levels of rotavirus thermostability enhancement. In the context of these formulations comprising magnesium ions, arginine provided the highest average level of thermostability enhancement.

Example 3: Stability of Rotavirus Formulations Comprising Arginine and/or Histidine After Storage for 4, 8 and 10 Weeks at 37° C.

Figure 5:
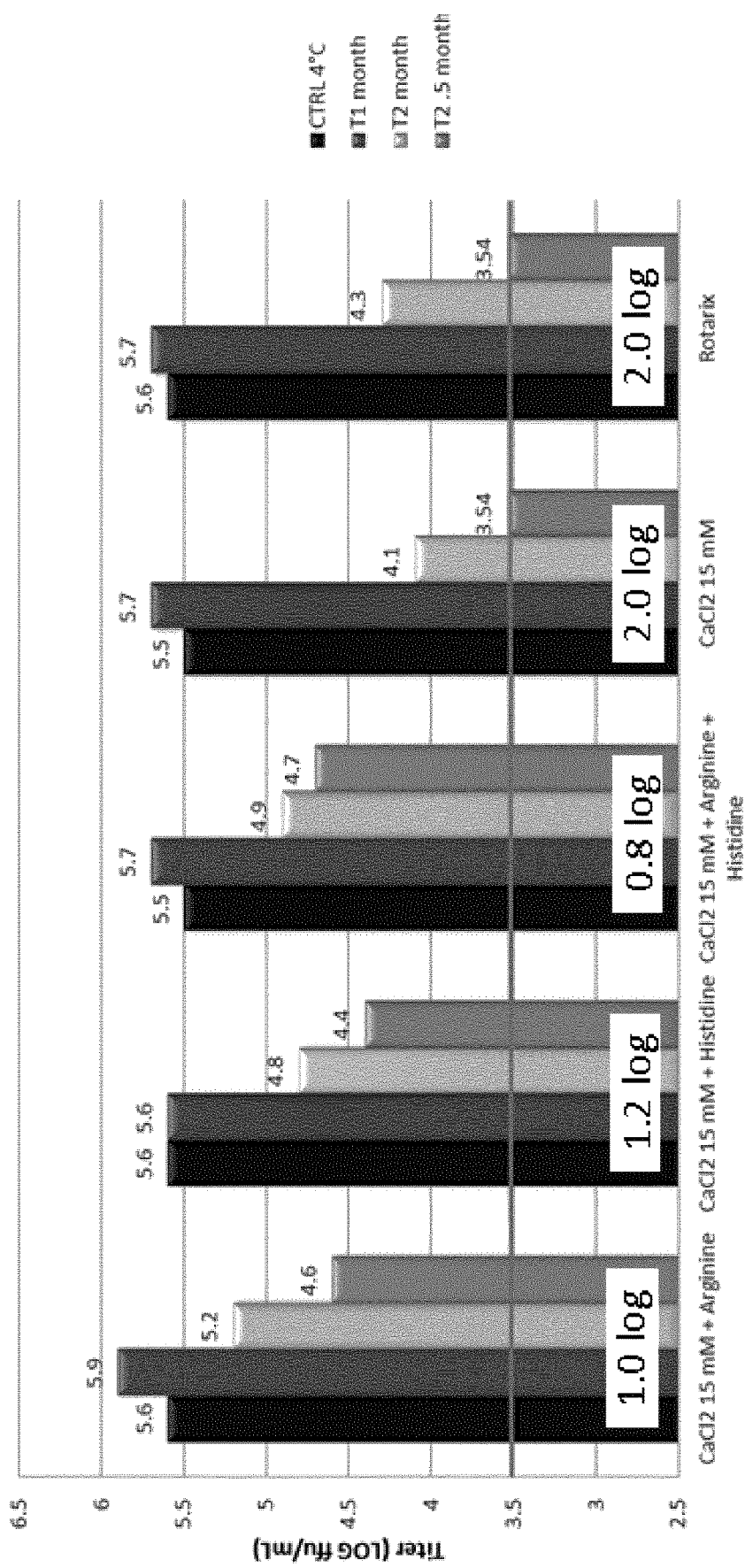
FIG. 5—Thermostability impact of arginine and/or histidine after storage for 4, 8 and 10 weeks at 37° C.

New batches of the formulations from Example 2 comprising histidine and/or arginine were prepared and stored at 37° C. for 4, 8 and 10 weeks (indicated as 1 month, 2 months, and 2.5 months, respectively, in FIG. 5), alongside reference formulations comprising (a) calcium chloride but no amino acids and (b) bench-prepared Rotarix vaccine (which comprises no calcium ions and no added amino acids). The LOG ffu/ml of each of these formulations at each of these timepoints is shown in FIG. 5. In parallel, a control formulation corresponding to each formulation was also assayed at 4° C. The difference in LOG ffu/ml between each control reading and the 10 week time point for each formulation is shown in a box below each data set. The viral titer of the reference formulations after 10 weeks is highlighted by the horizontal line. It can be seen from FIG. 5 that the addition of histidine and/or arginine to these formulations resulted in a surprising improvement in rotavirus stability compared to the reference formulations.

Example 4: Stability of Rotavirus Formulations Further Comprising Various Antioxidants and Proteins Formulations according to Examples 1 to 3 above were modified by addition of one of the following further components each: vitamin E succinate (VES), heparin, monothioglycerol (MTG), lactalbumin hydrolysate, albumin, or β casein.

Each formulation contained quantities of each component as set out in Table 3 in a volume of 1.4 ml and at a pH of 6.5. Six replicates of each formulation were tested. The thermostability of each formulation was assessed by measuring LOG ffu/ml of rotavirus after storage for 10 days at 45° C.

TABLE 3

| No. | Buffer Type | Conc. (w/v) | Polyol | Conc. (w/v) | Divalent cation | Conc. | Amino Acid | Conc. | Protein or antioxidant | Conc. |
|---|---|---|---|---|---|---|---|---|---|---|
| 1 | Adipic acid | 6.70% | Sucrose | 30% | Calcium | 15 mM | Arginine | 0.10% | VES | 0.9 mM |
| 2 | Adipic acid | 6.70% | Sucrose | 30% | Calcium | 15 mM | Histidine | 0.10% | VES | 0.9 mM |
| 3 | Adipic acid | 6.70% | Sucrose | 30% | CTRL | — | CTRL | — | VES | 0.9 mM |
| 4 | Adipic acid | 6.70% | Sucrose | 30% | Calcium | 15 mM | Arginine | 0.10% | Heparin | 0.10% |
| 5 | Adipic acid | 6.70% | Sucrose | 30% | Calcium | 15 mM | Histidine | 0.10% | Heparin | 0.10% |
| 6 | Adipic acid | 6.70% | Sucrose | 30% | CTRL | — | CTRL | — | Heparin | 0.10% |
| 7 | Adipic acid | 6.70% | Sucrose | 30% | Calcium | 15 mM | Arginine | 0.10% | MTG | 0.25% |
| 8 | Adipic acid | 6.70% | Sucrose | 30% | Calcium | 15 mM | Histidine | 0.10% | MTG | 0.25% |
| 9 | Adipic acid | 6.70% | Sucrose | 30% | CTRL | — | CTRL | — | MTG | 0.25% |
| 10 | Adipic acid | 6.70% | Sucrose | 30% | Calcium | 15 mM | Arginine | 0.10% | Lactalbumin hydrolysate | 0.10% |
| 11 | Adipic acid | 6.70% | Sucrose | 30% | Calcium | 15 mM | Histidine | 0.10% | Lactalbumin hydrolysate | 0.10% |
| 12 | Adipic acid | 6.70% | Sucrose | 30% | CTRL | — | CTRL | — | Lactalbumin hydrolysate | 0.10% |
| 13 | Adipic acid | 6.70% | Sucrose | 30% | Calcium | 15 mM | Arginine | 0.10% | Albumin | 0.10% |
| 14 | Adipic acid | 6.70% | Sucrose | 30% | Calcium | 15 mM | Histidine | 0.10% | Albumin | 0.10% |
| 15 | Adipic acid | 6.70% | Sucrose | 30% | CTRL | — | CTRL | — | Albumin | 0.10% |
| 16 | Adipic acid | 6.70% | Sucrose | 30% | Calcium | 15 mM | Arginine | 0.10% | B casein | 0.036% |
| 17 | Adipic acid | 6.70% | Sucrose | 30% | Calcium | 15 mM | Histidine | 0.10% | B casein | 0.036% |
| 18 | Adipic acid | 6.70% | Sucrose | 30% | CTRL | — | CTRL | — | B casein | 0.036% |
| 19 | Adipic acid | 6.70% | Sucrose | 30% | Calcium | 15 mM | Arginine | 0.10% | CTRL | — |
| 20 | Adipic acid | 6.70% | Sucrose | 30% | Calcium | 15 mM | Histidine | 0.10% | CTRL | — |
| 21 | Adipic acid | 6.70% | Sucrose | 30% | CTRL | — | CTRL | — | CTRL | — |
| 22 | CTRL 72% stressed | 6.70% | Sucrose | 72% | — | — | — | — | — | — |

Figure 6:
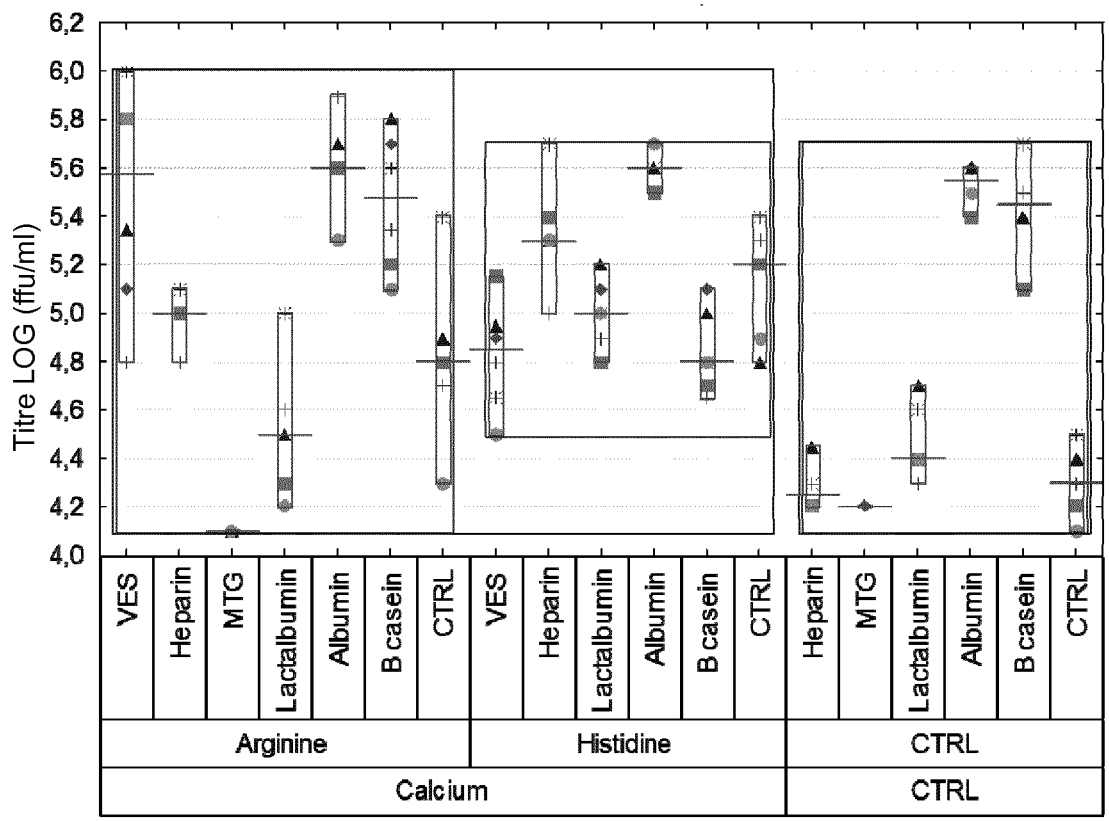
FIG. 6—Thermostability impact of various antioxidants and proteins after 10 days at 45° C.

The results are shown in FIG. 6. Boxes indicate different groupings of formulations. It can be seen from FIG. 6 that, in particular, the addition of albumin generally enhanced the thermostability of these formulations on average. The enhancing effect was visible both in the presence and in the absence of arginine, histidine and/or calcium.

Example 5: Further Enhancement of Rotavirus Formulation Thermostability

A suite of tests were performed in an attempt to identify a quadratic model of the impact of seven parameters (presence and concentration of sucrose, calcium, histidine, arginine, TPGS and albumin, and pH level) on thermostability of rotavirus formulations.

46 test formulations were prepared alongside 7 control formulations and 3 placebo formulations. Each formulation is labelled with a number (#). Control formulations (#1, 2, 32, 33, 34, 35 and 37) were assayed after storage for 14 days at 4° C. Placebo formulations contained no rotavirus. 50 mL of each formulation was prepared and three replicates of 1.4 ml of each formulation were tested for stability. In each formulation, the concentration of adipic acid was 6.7% w/v. Table 4 below provides details on every formulation. Percentages are weight/volume.

TABLE 4

| # | Active/ Placebo | Sucrose (%) | Calcium (mM) | Magnesium (mM) | His (%) | Arg (%) | TPGS (mM) | Albumin (r-HSA) (%) | pH |
|---|---|---|---|---|---|---|---|---|---|
| 1 | Active | 72 | 0 | 0 | 0 | 0 | 0 | 0 | 6.5 |
| 2 | Active | 72 | 15 | 0 | 0 | 0.1 | 0 | 0 | 6.5 |
| 3 | Placebo | 72 | 15 | 0 | 0 | 0.1 | 0 | 0 | 6.5 |
| 4 | Active | 72 | 5 | 0 | 0 | 0 | 0 | 0 | 7 |
| 5 | Active | 72 | 5 | 0 | 0 | 0 | 2 | 0.2 | 7 |
| 6 | Active | 72 | 5 | 0 | 0 | 0.1 | 0 | 0 | 6 |
| 7 | Active | 72 | 5 | 0 | 0 | 0.2 | 2 | 0 | 7 |
| 8 | Active | 72 | 5 | 0 | 0.1 | 0 | 0 | 0.2 | 6 |
| 9 | Active | 72 | 5 | 0 | 0.2 | 0 | 1 | 0.1 | 7 |
| 10 | Active | 72 | 5 | 0 | 0.2 | 0 | 2 | 0 | 6 |
| 11 | Active | 72 | 5 | 0 | 0.2 | 0.1 | 0 | 0.2 | 7 |
| 12 | Active | 72 | 5 | 0 | 0.2 | 0.2 | 1 | 0 | 6.5 |
| 13 | Active | 72 | 5 | 0 | 0.2 | 0.2 | 2 | 0.2 | 6 |
| 14 | Active | 72 | 10 | 0 | 0 | 0.2 | 1 | 0.2 | 7 |
| 15 | Active | 72 | 10 | 0 | 0.1 | 0.1 | 2 | 0 | 7 |
| 16 | Active | 72 | 10 | 0 | 0.2 | 0.2 | 0 | 0.1 | 6 |
| 17 | Active | 72 | 15 | 0 | 0 | 0 | 0 | 0.2 | 7 |
| 18 | Active | 72 | 15 | 0 | 0 | 0 | 2 | 0.2 | 6 |
| 19 | Active | 72 | 15 | 0 | 0 | 0.2 | 0 | 0 | 7 |
| 20 | Active | 72 | 15 | 0 | 0 | 0.2 | 2 | 0 | 6 |
| 21 | Active | 72 | 15 | 0 | 0.1 | 0.2 | 0 | 0.2 | 6.5 |
| 22 | Active | 72 | 15 | 0 | 0.2 | 0 | 0 | 0 | 6 |
| 23 | Active | 72 | 15 | 0 | 0.2 | 0 | 2 | 0 | 7 |
| 24 | Active | 72 | 15 | 0 | 0.2 | 0.1 | 1 | 0.2 | 6 |
| 25 | Active | 72 | 15 | 0 | 0.2 | 0.2 | 2 | 0.2 | 7 |
| 26 | Active | 51 | 5 | 0 | 0 | 0.2 | 0 | 0.2 | 6 |
| 27 | Active | 51 | 5 | 0 | 0.2 | 0.2 | 0 | 0 | 7 |
| 28 | Active | 51 | 10 | 0 | 0.1 | 0.1 | 1 | 0.1 | 6.5 |
| 29 | Active | 51 | 10 | 0 | 0.2 | 0 | 2 | 0.2 | 6.5 |
| 30 | Active | 51 | 15 | 0 | 0 | 0 | 1 | 0 | 6 |
| 31 | Active | 51 | 15 | 0 | 0 | 0.1 | 2 | 0.1 | 7 |
| 32 | Active | 30 | 15 | 0 | 0.1 | 0 | 0 | 0 | 6.5 |
| 33 | Active | 30 | 15 | 0 | 0 | 0.1 | 0 | 0 | 6.5 |
| 34 | Active | 30 | 15 | 0 | 0 | 0.1 | 1 | 0 | 6.5 |
| 35 | Active | 30 | 5 | 0 | 0 | 0 | 0 | 0 | 6 |
| 36 | Placebo | 30 | 5 | 0 | 0 | 0 | 0 | 0 | 6 |
| 37 | Active | 30 | 5 | 0 | 0 | 0 | 0 | 0 | 7 |
| 38 | Placebo | 30 | 5 | 0 | 0 | 0 | 0 | 0 | 7 |
| 39 | Active | 30 | 5 | 0 | 0 | 0 | 0 | 0.2 | 7 |
| 40 | Active | 30 | 5 | 0 | 0 | 0 | 2 | 0.2 | 6 |
| 41 | Active | 30 | 5 | 0 | 0 | 0.2 | 0 | 0.1 | 6.5 |
| 42 | Active | 30 | 5 | 0 | 0 | 0.2 | 2 | 0 | 6 |
| 43 | Active | 30 | 5 | 0 | 0.2 | 0 | 0 | 0 | 6 |
| 44 | Active | 30 | 5 | 0 | 0.2 | 0 | 2 | 0 | 7 |
| 45 | Active | 30 | 5 | 0 | 0.2 | 0.2 | 0 | 0.2 | 6 |
| 46 | Active | 30 | 5 | 0 | 0.2 | 0.2 | 2 | 0.2 | 7 |
| 47 | Active | 30 | 10 | 0 | 0 | 0.2 | 1 | 0 | 7 |
| 48 | Active | 30 | 15 | 0 | 0 | 0 | 0 | 0.2 | 6 |
| 49 | Active | 30 | 15 | 0 | 0 | 0 | 2 | 0 | 6.5 |
| 50 | Active | 30 | 15 | 0 | 0 | 0.2 | 2 | 0.2 | 6 |
| 51 | Active | 30 | 15 | 0 | 0.1 | 0 | 2 | 0.2 | 7 |
| 52 | Active | 30 | 15 | 0 | 0.1 | 0.2 | 0 | 0 | 6 |
| 53 | Active | 30 | 15 | 0 | 0.2 | 0 | 0 | 0 | 7 |
| 54 | Active | 30 | 15 | 0 | 0.2 | 0 | 2 | 0.1 | 6 |
| 55 | Active | 30 | 15 | 0 | 0.2 | 0.2 | 0 | 0.2 | 7 |
| 56 | Active | 30 | 15 | 0 | 0.2 | 0.2 | 2 | 0 | 6.5 |

The mean thermostability of each test formulation was assessed by measuring LOG ffu/ml of rotavirus after storage for 14 days at 45° C.

Figure 7:
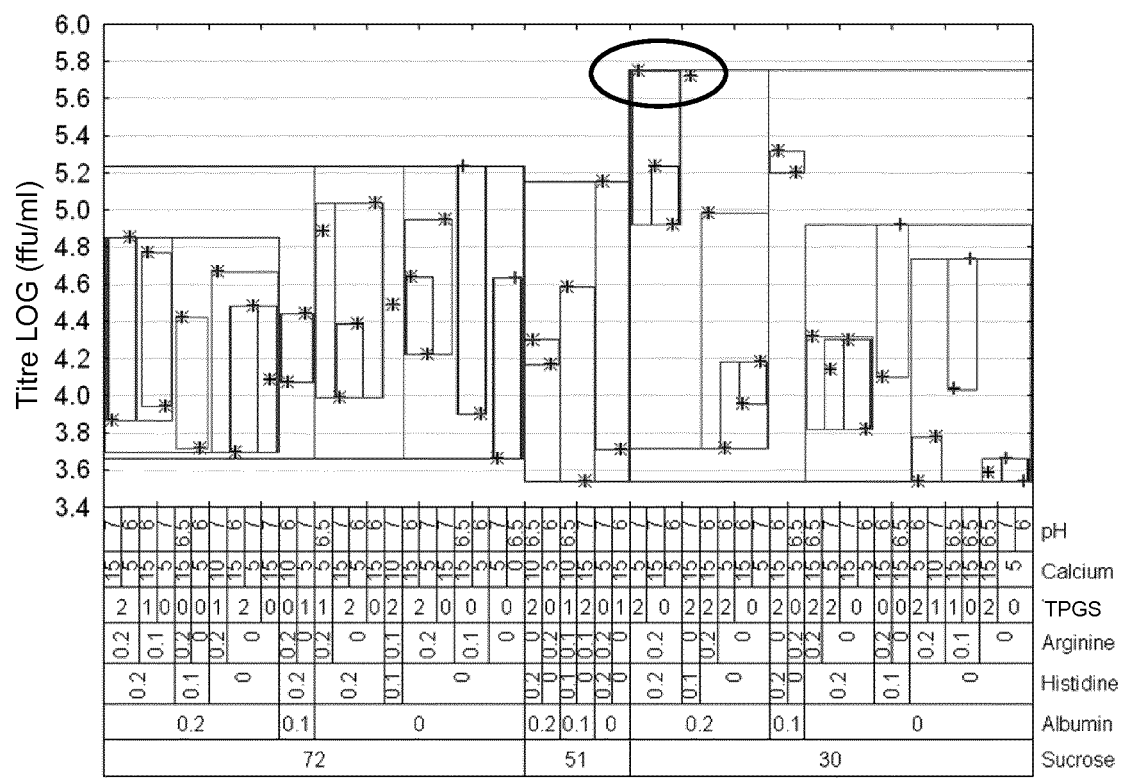
FIG. 7—Thermostability of multiple formulations with varied parameters after 14 days at 45° C.

The results of the 14 day storage tests are shown in FIGS. 7-12. FIG. 7 provides thermostability results in respect of all tested parameters after 14 days storage at 45° C. and FIGS. 8-12 each more closely illustrate particular aspects of these same data. Control formulations are denoted by plus sign (+). Tables 5, 6 and 7 below repeat the formulation details in Table 4 but set out in line with the arrangement of FIG. 7.

TABLE 5

SUCROSE 72% w/v

| Sucrose (% w/v) | Albumin (% w/v) | Histidine (% w/v) | Arginine (% w/v) | TPGS (mM) | Calcium (mM) | pH |
|---|---|---|---|---|---|---|
| 72 | 0.2 | 0.2 | 0.2 | 2 | 15 | 7 |
|  |  |  |  |  | 5 | 6 |
|  |  |  | 0.1 | 1 | 15 | 6 |
|  |  |  | 0 | 0 | 5 | 7 |
|  |  | 0.1 | 0.2 | 0 | 15 | 6.5 |
|  |  |  | 0 | 0 | 5 | 6 |
|  |  | 0 | 0.2 | 1 | 10 | 7 |
|  |  |  | 0 | 2 | 15 | 6 |
|  |  |  |  |  | 5 | 7 |
|  |  |  |  | 0 | 15 | 7 |
|  | 0.1 | 0.2 | 0.2 | 0 | 10 | 6 |
|  |  |  | 0 | 1 | 5 | 7 |
|  | 0 | 0.2 | 0.2 | 1 | 5 | 6.5 |
|  |  |  | 0 | 2 | 15 | 7 |
|  |  |  |  |  | 5 | 6 |
|  |  |  |  | 0 | 15 | 6 |
|  |  | 0.1 | 0.1 | 2 | 10 | 7 |
|  |  | 0 | 0.2 | 2 | 15 | 6 |
|  |  |  | 0.2 | 2 | 5 | 7 |
|  |  |  |  | 0 | 15 | 7 |
|  |  |  | 0.1 | 0 | 15 | 6.5 |
|  |  |  |  |  | 5 | 6 |
|  |  |  | 0 | 0 | 5 | 7 |
|  |  |  |  |  | 0 | 6.5 |

TABLE 6

SUCROSE 51% w/v

| Sucrose | Albumin | Histidine | Arginine | TPGS | Calcium | pH |
|---|---|---|---|---|---|---|
| 51 | 0.2 | 0.2 | 0 | 2 | 10 | 6.5 |
|  | 0 | 0.2 | 0 | 5 | 6 |
|  | 0.1 | 0.1 | 0.1 | 1 | 10 | 6.5 |
|  | 0 | 0.1 | 2 | 15 | 7 |
|  | 0 | 0.2 | 0.2 | 0 | 5 | 7 |
|  | 0 | 0 | 1 | 15 | 6 |

TABLE 7

SUCROSE 30% w/v

| Sucrose % w/v | Albumin % w/v | Histidine % w/v | Arginine % w/v | TPGS mM | Calcium mM | pH |
|---|---|---|---|---|---|---|
| 30 | 0.2 | 0.2 | 0.2 | 2 | 5 | 7 |
|  |  |  | 0 | 0 | 15 | 7 |
|  |  |  |  |  | 5 | 6 |
|  |  | 0.1 | 0 | 2 | 15 | 7 |
|  |  | 0 | 0.2 | 2 | 15 | 6 |
|  |  | 0 | 0 | 2 | 5 | 6 |
|  |  |  |  | 0 | 15 | 6 |
|  |  |  |  |  | 5 | 7 |
|  | 0.1 | 0.2 | 0 | 2 | 15 | 6 |
|  |  | 0 | 0.2 | 0 | 5 | 6.5 |
|  | 0 | 0.2 | 0.2 | 2 | 15 | 6.5 |
|  |  |  | 0 | 2 | 5 | 7 |

TABLE 7-continued

SUCROSE 30% w/v

| Sucrose % w/v | Albumin % w/v | Histidine % w/v | Arginine % w/v | TPGS mM | Calcium mM | pH |
|---|---|---|---|---|---|---|
|  |  |  |  | 0 | 15 | 7 |
|  |  |  |  |  | 5 | 6 |
|  | 0.1 | 0.2 | 0 | 0 | 15 | 6 |
|  |  | 0 | 0 | 0 | 15 | 6.5 |
|  | 0 | 0.2 | 0 | 2 | 5 | 6 |
|  |  |  | 1 | 10 | 7 |
|  | 0.1 | 1 | 15 | 6.5 |
|  |  | 0 | 15 | 6.5 |
|  | 0 | 2 | 15 | 6.5 |
|  |  | 0 | 5 | 7 |
|  |  |  |  |  |  | 6 |

It can be seen from FIG. 7 that, in particular, the formulations comprising low (30% w/v) sucrose, calcium ions, plus histidine and/or arginine were especially effective, maintaining high titres after 14 days storage. The two most effective formulations (circled) providing the highest viral titres contained (a) 30% w/v sucrose, 15 mM calcium ions, 0.1% w/v histidine, 0% w/v arginine, 2 mM TPGS and 0.2% w/v recombinant human serum albumin; and (b) 30% w/v sucrose, 5 mM calcium ions, 0.2% w/v histidine, 0.2% w/v arginine, 2 mM TPGS and 0.2% w/v recombinant human serum albumin; both formulations having a pH of 7.

Interactions Between Components

Figure 8:
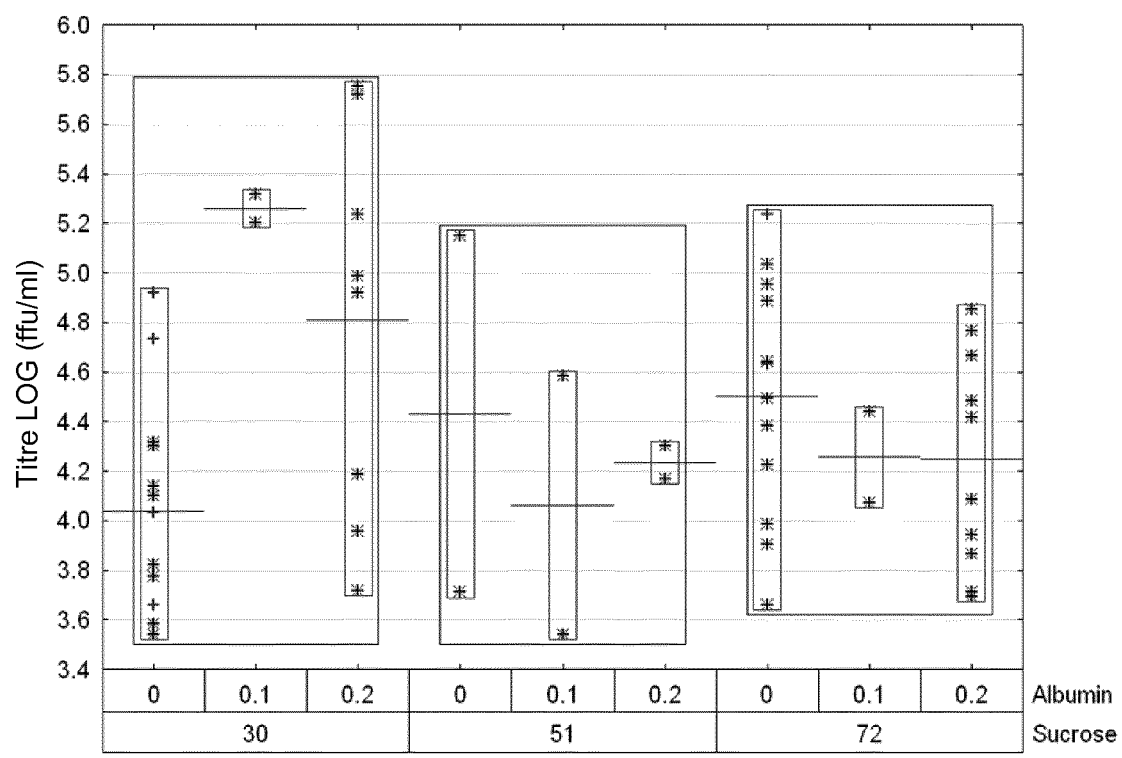
FIG. 8—Albumin and sucrose relationship after 14 days at 45° C.

FIG. 8 illustrates the interaction between albumin and sucrose specifically. It can be seen from FIG. 8 that at both 72% and 51% w/v sucrose, the addition of albumin to these formulations made no impact or a small detrimental impact to mean viral titre. In contrast, at 30% w/v sucrose, the presence of albumin resulted in higher mean viral tires. It appears that the thermostability improvements to these formulations provided by the addition of albumin are negated by the addition of high levels of sucrose.

Figure 9:
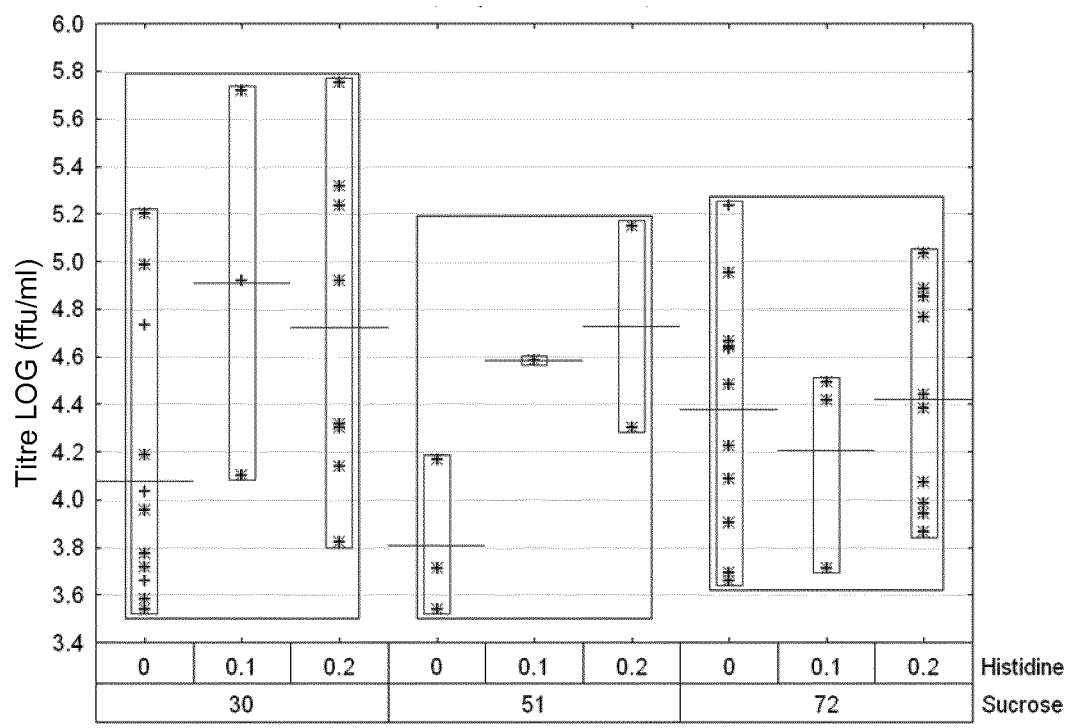
FIG. 9—Histidine and sucrose relationship after 14 days at 45° C.

FIG. 9 illustrates the interaction between histidine and sucrose specifically. It can be seen from FIG. 9 that higher quantities of histidine generally provide improved average viral titres, regardless of sucrose concentration at 30, 51 or 72% w/v. However, the highest viral titre readings were achieved in formulations with histidine present at 30% w/v sucrose concentration.

Figure 10:
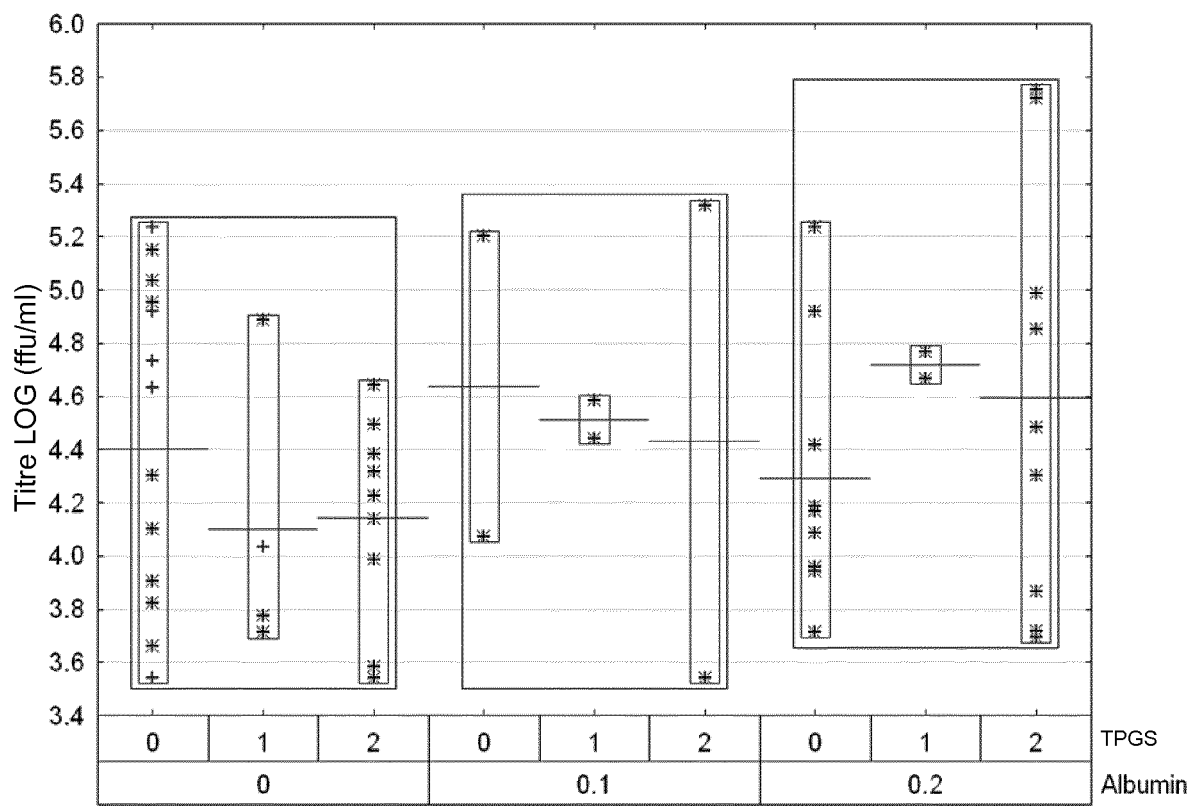
FIG. 10—TPGS and albumin relationship after 14 days at 45° C.

FIG. 10 illustrates the interaction between TPGS and albumin specifically. It can be seen from FIG. 10 that higher levels of both TPGS and albumin both generally improved thermostability.

Figure 11:
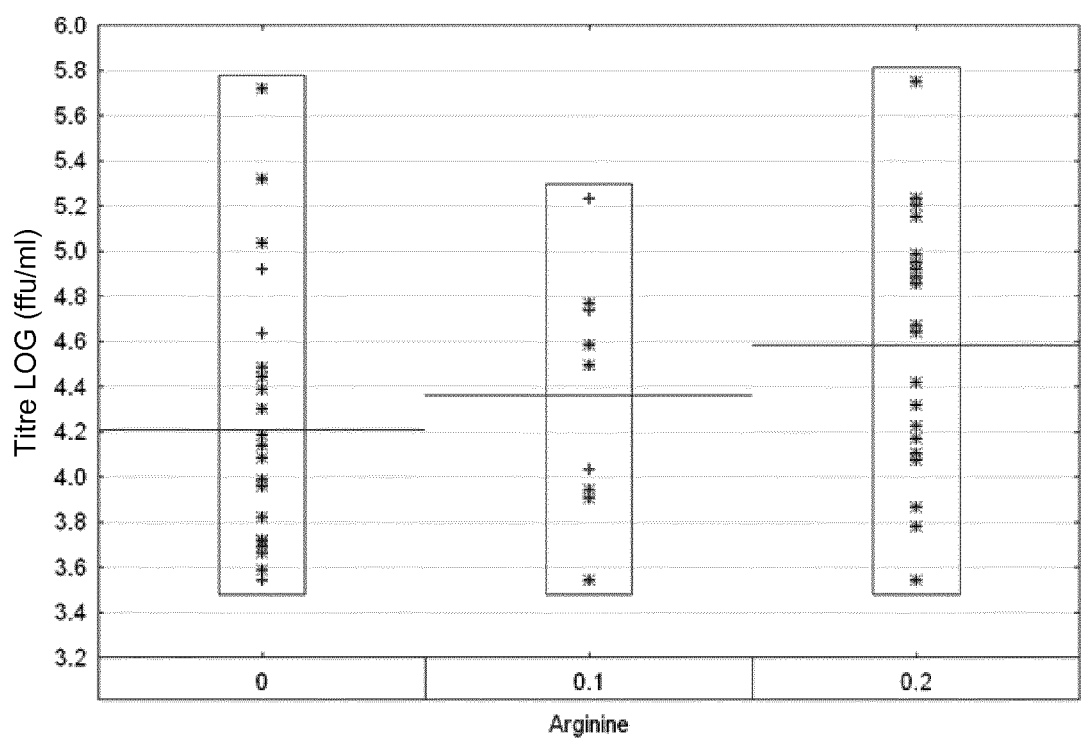
FIG. 11—Thermostability impact of increasing arginine concentration after 14 days at 45° C.

FIG. 11 illustrates the impact of increasing levels of arginine on the tested formulations. It can be seen from FIG. 11 that higher levels of arginine generally improved mean viral titre.

Figure 12:
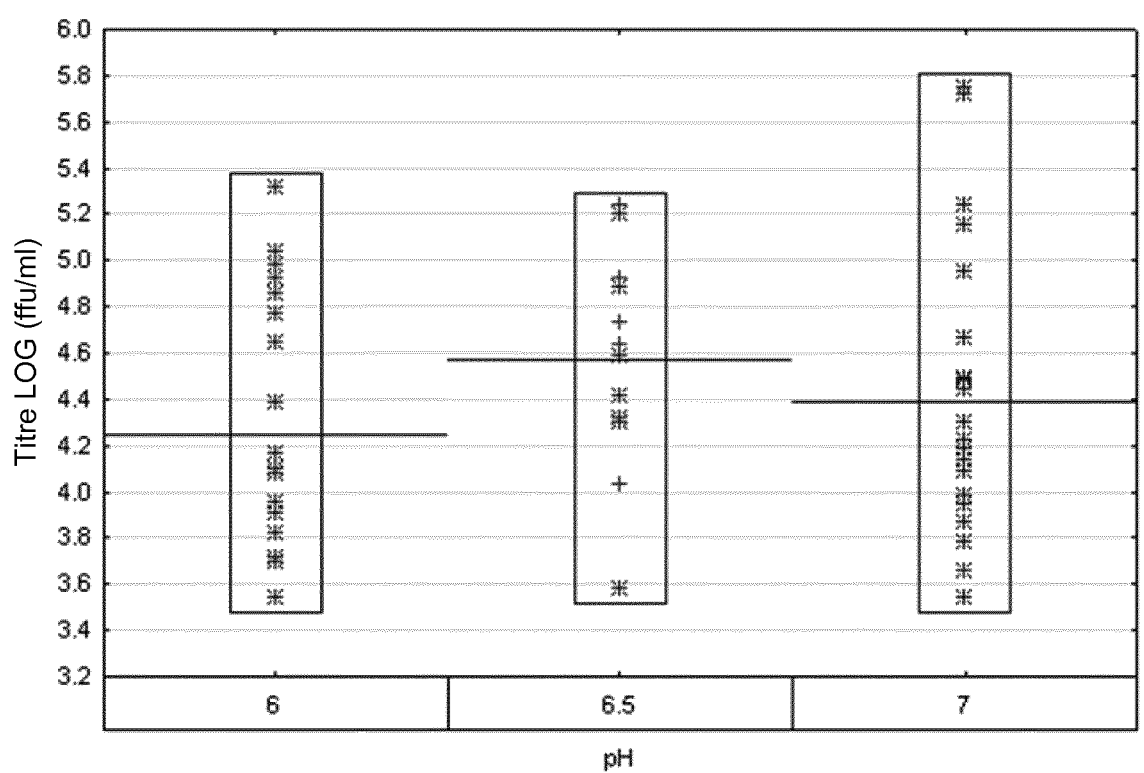
FIG. 12—Thermostability impact of varied pH after 14 days at 45° C.

FIG. 12 illustrates the impact of pH variation on the tested formulations. It can be seen from FIG. 12 that from amongst pH 6, 6.5 and 7, the highest viral titres are generally achieved at pH 6.5.

Example 6: A Highly Thermostable Formulation

A composition was formulated comprising 6.7% adipate buffer, 10% w/v sucrose, 5 mM calcium ions, 0.2% w/v histidine, 0.2% w/v arginine, 0.2% w/v recombinant human serum albumin (rHSA), 1 mM TPGS and having a pH of 6.5. The composition was produced in two separate lots. The thermostability of this formulation was assessed alongside commercially available Rotarix over a period of 8 weeks storage at 40° C. Commercially available Rotarix differs from the bench-prepared Rotarix used in Examples 1-5 in the manner detailed in Example 1.

Figure 13:
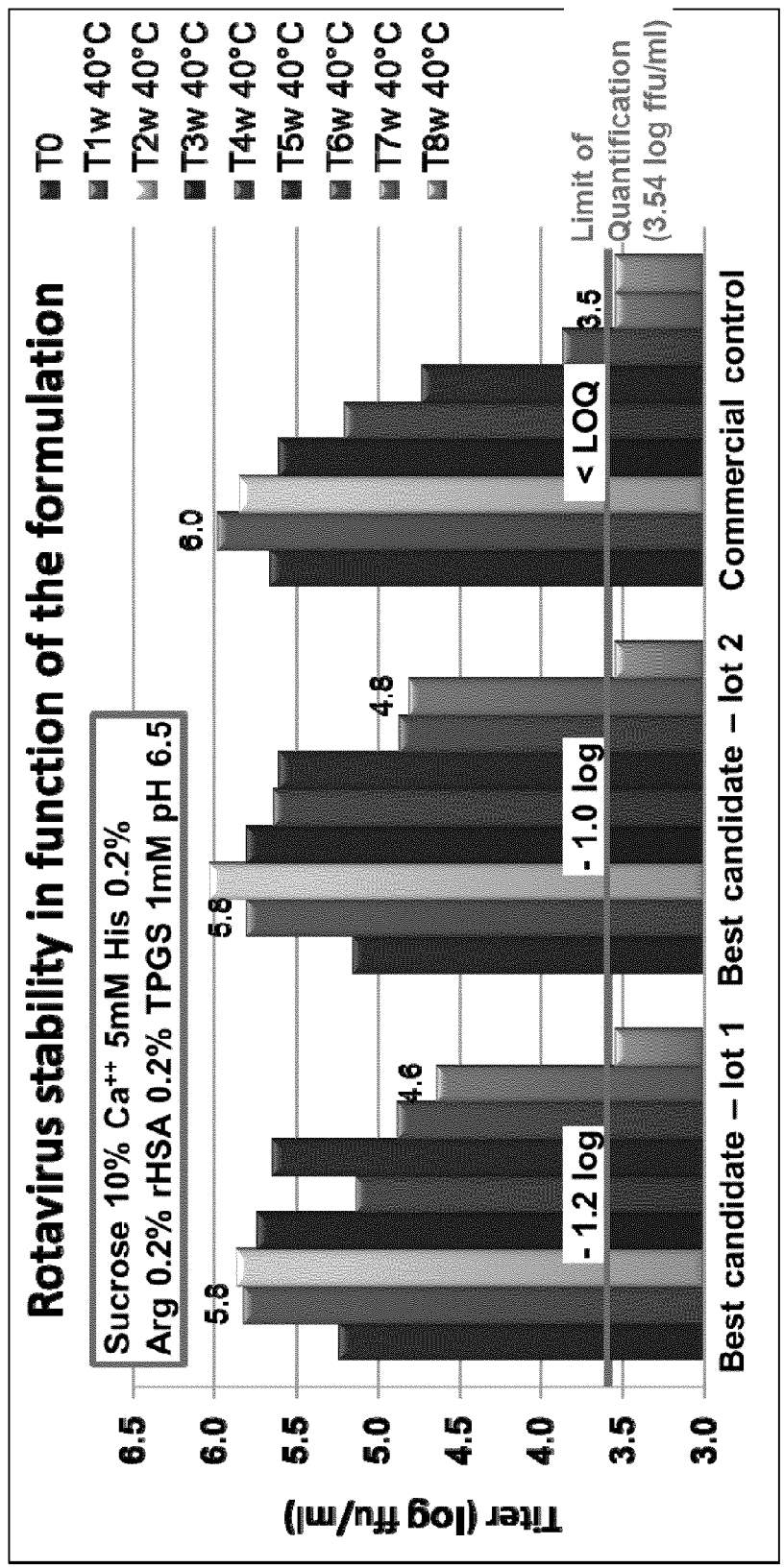
FIG. 13—Thermostability of a formulation comprising 10% w/v sucrose, 5 mM calcium ions, 0.2% w/v histidine, 0.2% w/v arginine, 0.2% w/v recombinant human serum albumin, 1 mM TPGS and having a pH of 6.5, after storage at 45° C.

Titre readings were taken at the start of the assay (T0) and every week thereafter. The results are shown in FIG. 13. In FIG. 13, for each of lot 1, lot 2 and the commercial control, the columns from left to right are T0,T1w 40° C., T2w 40° C., T3w 40° C., T4w 40° C., T5w 40° C., T6w 40° C., T7w 40° C. and T8w 40° C. It can be seen from FIG. 13 that after 7 weeks, this exemplary formulation lost approximately 1 log of viral titre, while the viral titre dropped below the limit of quantification in the Rotarix control after the same time period.

The invention claimed is:

1. A thermostable liquid immunogenic composition comprising:
 a human live attenuated rotavirus,
 sucrose,
 adipic acid,
 calcium ions,
 histidine, and
 vitamin E succinate (VES);
 wherein said immunogenic composition is in the form of liquid formulations;
 wherein said composition has a level of thermostability such that, after storage of the composition for 2.5 months at 37° C., the composition has a maximum virus titer loss of 1.5, as expressed in log10 ffu/mL as compared to the composition's initial virus titer before storage;
 wherein
  rotavirus is present at an initial titer ranging from $1\times10^5$ to $1\times10^8$ pfu/mL;
  the concentration of sucrose is 10% w/v;
  the adipic acid is present at a concentration of 6.7% w/v;
  the calcium ions are present at a concentration from 5 mM;
  the VES is present at a concentration of no more than 1.5 mM;
  the histidine is present at a concentration of 0.2%;
  the arginine is present at a concentration of 0.2% w/v.

2. The immunogenic composition according to claim 1, wherein the pH of the immunogenic composition is between about pH 6.0 and about pH 7.0.

3. The immunogenic composition according to claim 1 further comprising a protein, wherein the protein is albumin at a concentration of at least 0.05% w/v.

4. The immunogenic composition according to claim 1 wherein the immunogenic composition is provided in a dose volume of 0.2 ml to 2.0 ml.

5. The immunogenic composition according to claim 1 wherein the immunogenic composition is suitable for oral administration.

6. The immunogenic composition according to claim 1, which is a vaccine.

7. A pharmaceutical composition comprising the immunogenic composition according to claim 1 and an additional pharmaceutically acceptable excipient.

8. A kit comprising the immunogenic composition or a pharmaceutical composition according to claim 1 and instructions for use of the kit.

9. A method for the preparation of an immunogenic composition according to claim 1, comprising admixing
 a rotavirus,
  a sugar and/or polyol,
  an adipate buffer,
  calcium ions, and
  histidine.

10. The immunogenic composition according to claim 3 further comprising a protein, wherein the protein is human serum albumin at a concentration of at least 0.05% w/v.

11. The immunogenic composition according to claim 3 further comprising a protein, wherein the protein is recombinant human serum albumin at a concentration of at least 0.05% w/v.

* * * * *